US008394612B2

(12) United States Patent
Imaizumi et al.

(10) Patent No.: US 8,394,612 B2
(45) Date of Patent: Mar. 12, 2013

(54) METHOD FOR PRODUCTION OF AN L-AMINO ACID

(75) Inventors: Akira Imaizumi, Kawasaki (JP); Larisa Gotlibovna Airikh, Moscow region (RU); Vera Georgievna Doroshenko, Moscow (RU); Irina Sergeevna Tsyrenzhapova, Buryatia (RU)

(73) Assignee: Ajinomoto Co., Inc., Tokyo (JP)

( * ) Notice: Subject to any disclaimer, the term of this patent is extended or adjusted under 35 U.S.C. 154(b) by 650 days.

(21) Appl. No.: 12/184,637

(22) Filed: Aug. 1, 2008

(65) Prior Publication Data
US 2010/0184162 A1 Jul. 22, 2010

Related U.S. Application Data

(63) Continuation of application No. PCT/JP2007/051815, filed on Feb. 2, 2007.

(30) Foreign Application Priority Data

Feb. 2, 2006 (JP) ................................. 2006-025620

(51) Int. Cl.
C12P 13/22 (2006.01)

(52) U.S. Cl. ......... 435/108; 435/106; 435/110; 435/115

(58) Field of Classification Search .................. None
See application file for complete search history.

(56) References Cited

U.S. PATENT DOCUMENTS

| | | | |
|---|---|---|---|
| 5,661,012 A | 8/1997 | Sano et al. | |
| 5,763,230 A | 6/1998 | De Hollander et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 5,939,307 A | 8/1999 | Wang et al. | |
| 6,040,160 A | 3/2000 | Kojima et al. | |
| 6,090,597 A * | 7/2000 | Hirano et al. | 435/115 |
| 6,960,455 B2 | 11/2005 | Livshits et al. | |
| 7,090,998 B2 | 8/2006 | Ishikawa et al. | |
| 7,179,623 B2 | 2/2007 | Livshits et al. | |
| 7,259,003 B2 | 8/2007 | Livshits et al. | |
| 7,306,933 B2 | 12/2007 | Dien et al. | |
| 2002/0155556 A1 | 10/2002 | Imaizumi et al. | |
| 2002/0160461 A1 | 10/2002 | Nakai et al. | |
| 2004/0265956 A1 | 12/2004 | Takikawa et al. | |
| 2005/0079571 A1 | 4/2005 | Collier et al. | |
| 2005/0106688 A1 | 5/2005 | Imaizumi et al. | |
| 2005/0191684 A1 | 9/2005 | Zimenkov et al. | |
| 2006/0019355 A1 | 1/2006 | Ueda et al. | |
| 2006/0063240 A1 | 3/2006 | Katashkina et al. | |
| 2006/0088919 A1 | 4/2006 | Rybak et al. | |
| 2008/0153138 A1 | 6/2008 | Livshits et al. | |

FOREIGN PATENT DOCUMENTS

| | | |
|---|---|---|
| EP | 0488424 | 6/1992 |
| JP | 2002-153285 | 5/2002 |
| WO | WO01/53459 | 7/2001 |
| WO | WO2005/087802 | 9/2005 |

OTHER PUBLICATIONS

Imaizumi et al., Journal of Biotechnology, 2005, vol. 117, p. 111-118.*
Makino et al., J Mol Biol, 1986, vol. 190, No. 1, Abstract.*
Laird, M. W., et al., "Optimization of BLyS production and purification from *Escherichia coli*," Protein Expression and Purification 2005;39:237-246.
Makino, K., et al., "Nucleotide Sequence of the *phoB* Gene, the Positive Regulatory Gene for the Phosphate Regulon of *Escherichia coli* K-12," J. Mol. Biol. 1986;190:37-44.
Silen, Jr. L., et al., "Analysis of Prepro-α-Lytic Protease Expression in *Escherichia coli* Reveals that the Pro Region Is Required for Activity," J. Bacteriol. 1989;171(3):1320-1325.
International Search Report for PCT Patent App. No. PCT/JP2007/051815 (Apr. 17, 2007).
Goldstein, M. A., et al., "Prokaryotic promoters in biotechnology," Biotechnol. Ann, Rev. 1995;1:105-128.
Torriani, A., "From Cell Membrane to Nucleotides: The Phosphate Regulon in *Escherichia coil*," BioEssays 1990;12(8):371-376.
Supplementary European Search Report for European Patent App. No. 07707964.8 (Oct. 2, 2009).
Bardin, S., et al., "A Phosphate Trat sport System Is Required for Symbiotic Nitrogen Fixation by *Rhizobium meliloti*," J. Bacteriol. 1996;178(15):4540-4547.
Basu, T., et al., "Over Expression of Inducible Proteins in *Escherichia coil* by Treatment With Ethanol," Biochem. Molecul. Biol. Internat'l 1997;41(6): 1093-1100.
Imaizumi, A., et al., "Improved Production of Enzymes, Which Are Expressed under the Pho Regulon Promoter, in the *rmf* Gene (encoding ribosome modulation factor) Disruptant of *Escherichia coli*," Biosci. Biotech. Biochem. 2006;70(4):949-957.
Kaderbhai, M. A., et al., "Targeting of Active Human Cytochrome P4501A1 (CYP1A1) to the Periplasmic Space of *Escherichia coli*," Biochemical and Biophysical Research Communications 2000;279:803-807.
Kaderbhai, M.A., et al., "Export of Cytochrome P450 105D1 to the Periplasmic Space of *Escherichia coil*," Appl. Environmen. Microbiol. 2001;67(5):2136-2138.

(Continued)

*Primary Examiner* — Kade Ariani

(74) *Attorney, Agent, or Firm* — Shell Guest Cermak; Cermak Nakajima LLP

(57) ABSTRACT

A method is provided for producing an L-amino acid by culturing a microorganism belonging to the Enterobacteriaceae family and having the ability to produce an L-amino acid, in a medium to produce and accumulate the L-amino acid in the medium. The microorganism has been modified by introduction of a DNA fragment which includes a pho regulon promoter and a structural gene encoding an L-amino acid biosynthetic enzyme, which is ligated downstream of the promoter so that the gene is expressed by the promoter, and so that the activity of the L-amino acid biosynthetic enzyme is increased by the expression of the gene by the promoter. In this way, the L-amino acid that is produced in the medium can be collected. Furthermore, the phosphorus concentration in the medium is such that the expression of the gene by the promoter is induced.

12 Claims, 3 Drawing Sheets

OTHER PUBLICATIONS

Karunakaran, T., et al., "Cloning and Expression in *Escherichia coli* of an Alkaline Phosphatase (*phoA*) Gene from *Zymomonas mobilis*," Curr. Microbial. 1992;25:291-295.

Kikuchi, Y., et al., "The nucleotide sequence of the promoter and the amino-terminal region of alkaline phosphatase structural gene (phoA) of *Escherichia coli*," Nuc. Acids Res. 1981;9(21):5671-5678.

Kim, S-K, et al., "Molecular Analysis of the *phoH* Gene, Belonging to the Phosphate Regulon in *Escherichia coli*," J. Bacteriol. 1993;175(5):1316-1324.

Kim, S-K, et al., "Dual Transcriptional Regulation of the *Escherichia coli* Phosphate-Starvation-Inducible *psiE* Gene of the Phosphate Regulon by PhoB and the Cyclic AMP (cAMP)-cAMP Receptor Protein Complex," J. Bacteriol. 2000;182(19):5596-5599.

Kopitar-Jerala, N., et al., "ReCombinant Anti-Stefin A $F_{ab}$ Fragment: Sequence Analysis of the Variable Region and Expression in *Escherichia coli*," Biol Chem 2000;381:1245-1249.

Kuroda, A., et al., "Evaluation of Phosphate Removal from Water by Immobilized Phosphate-Binding Protein PstS," J. Biosci. Bioeng. 2000;90(6):688-690.

Miksch, G., et al., "Factor that influence the extracellular expression of streptavidin in *Escherichia coli* using a bacteriocin release protein," Appl. Microbial. Biotechnol. 2008; 8 pp.

Nandineni, M. R., et al., "Evidence for an Arginine Exporter Encoded by *yggA* (*argO*) That Is Regulated by the LysR-Type Transcriptional Regulator ArgP in *Escherichia coli*," J. Bacteria 2004;186(11):3539-3546.

Schweizer, H., et al., "Mapping of Two *ugp* Genes Coding for the *pho* Regulon-Dependent *sn*-Glycerol-3-Phosphate Transport System of *Escherichia coli*," J. Bacterial. 1982;150(3):1164-1171.

Smith, M.W., et al., "Expression of periplasmic binding proteins for peptide transport is subject to negative regulation by phosphate limitation in *Escherichia coli*," FEMS Microbiol. Lett. 1992;100:183-190.

Suziedeliene, E., et al., "The Acid-Inducible *asr* Gene in *Escherichia coli*: Transcriptional Control by the *phoBR* Operon," J. Bacteriol. 1999;181(7):2084-2093.

Wanner, B. L., "Phosphorus Assimilation and Control of the Phosphate Regulon," *Escherichia coli* and *Salmonella*: Cellular and Molecular Biology, $2^{nd}$ Edition, Edited by Neidhardt, F. C., ASM Press, Washington, DC, 1996, pp. 1357-1381.

Wen, C., et al., "Construction of Secretory Expression System Suitable to Express Glucagon Under the Control of $P_1$, Promoter," Curr. Microbiol. 2003;47:180-185.

Xi, Q. S., et al., "Expression of Human Epiregulin in *E. coli*," Acta Biochemica et Biophysica Sinica 2000;32(3):295-298, with partial English translation.

Xu, R., et al., "High-Level Expression and Secretion of Recombinant Mouse Endostatin by *Escherichia coli*," Protein Expression and Purification 2002;24:453-459.

International Preliminary Report on Patentability for PCT Patent App. No. PCT/JP2007/051815 (Aug. 14, 2008).

U.S. Appl. No. 12/055,438, filed Mar. 26, 2008, Iwatani et al.

\* cited by examiner

MUD-*aroG4*-*pheA*$^B$ - *aroL*

MUD-(P$_{PhoA}$- *aroG4*)-*pheA*$^B$ -

METHOD FOR PRODUCTION OF AN L-AMINO ACID

This application is a continuation under 35 U.S.C. §120 to PCT Patent Application No. PCT/JP2007/051815, filed on Feb. 2, 2007, which claims priority under 35 U.S.C. §119 to Japanese Patent Application No. 2006-025620, filed Feb. 2, 2006, both of which are incorporated by reference. The Sequence Listing in electronic format filed herewith is also hereby incorporated by reference in its entirety (File Name: US-369_Seq_List_Copy__1; File Size: 54 KB; Date Created: Aug. 1, 2008).

BACKGROUND OF THE INVENTION

1. Technical Field

The present invention relates to a method for producing an L-amino acid using a microorganism, especially L-lysine, L-threonine, L-phenylalanine, and L-tryptophan. These are industrially useful L-amino acids, for example, L-lysine, L-threonine, and L-tryptophan are useful as additives in animal feed, ingredients in health food, for amino acid infusions, and so forth. L-phenylalanine is useful as a precursor of sweeteners, and so forth.

2. Background Art

L-amino acids are industrially produced by fermentation using a microorganism belonging to the genus *Brevibacterium, Corynebacterium, Escherichia*, or the like. In such production methods, strains isolated from nature or artificial variants of such strains are used, and further, microorganisms modified by recombinant DNA techniques so that the activity of basic L-amino acid biosynthetic enzymes are increased are used, and so forth (EP 0643135 B, EP 0733712 B, EP 1477565 A, EP 0796912 A, EP 0837134 A, WO 01/53459, EP 1170376 A, WO 2005/010175, WO 96/17930, and U.S. Pat. No. 5,763,230).

When a culture of bacteria is performed for the purpose of producing a substance, excessive proliferation of the microorganisms generally decreases distribution of substrates to the objective products, and therefore it may be necessary to restrict the addition of required nutrients in medium. Examples of the nutrients which may need to be restricted include the required amino acids and phosphorus. A method is described in EP 0643135 B, wherein excessive proliferation of bacteria is suppressed by maintaining the phosphorus concentration in the culture medium to a certain range.

SUMMARY OF THE INVENTION

An aspect of the present invention is to provide an improved method for producing an L-amino acid by fermentation.

It has been found that by introducing an expression construct which includes a pho regulon promoter sequence and a gene encoding an L-amino acid biosynthetic enzyme ligated downstream of the promoter into a microorganism belonging to the Enterobacteriaceae family, and culturing the microorganism in a medium containing a lower phosphorus concentration, production of the L-amino acid by the microorganism was improved.

It is an aspect of the present invention to provide a method for producing an L-amino acid comprising A) culturing in a medium a microorganism belonging to the Enterobacteriaceae family and having the ability to produce an L-amino acid, and B) collecting the L-amino acid from the medium, wherein a DNA fragment comprising: i) a pho regulon promoter, and ii) a structural gene encoding an L-amino acid biosynthetic enzyme, is introduced into said microorganism, wherein said gene is ligated downstream of the promoter so that the gene is expressed by the promoter, and wherein the activity of the L-amino acid biosynthetic enzyme is increased when the gene is expressed by the promoter, and wherein the phosphorus concentration in the medium is such that the expression of the gene by the promoter is induced.

It is a further aspect of the invention to provide the production method as described above, wherein the pho regulon promoter is a promoter of a gene selected from the group consisting of phoA, phoB, phoE, phoH, asr, argP, ugpB, pstS, psiE and phnC.

It is a further aspect of the invention to provide the production method as described above, wherein the pho regulon promoter comprises a pho box.

It is a further aspect of the invention to provide the production method as described above, wherein the phosphorus concentration in the medium is 200 μM/L or lower.

It is a further aspect of the invention to provide the production method as described above, wherein expression level of the L-amino acid biosynthetic enzyme decreases when phosphorus is depleted in the medium.

It is a further aspect of the invention to provide the production method as described above, wherein the DNA fragment is carried on a multi-copy vector in the microorganism, or is introduced into the chromosomal DNA of the microorganism.

It is a further aspect of the invention to provide the production method as described above, wherein the microorganism belonging to the Enterobacteriaceae family is selected from the group consisting of *Escherichia* bacteria, *Enterobacter* bacteria, *Pantoea* bacteria, *Klebsiella* bacteria, and *Serratia* bacteria.

It is a further aspect of the invention to provide the production method as described above, wherein the L-amino acid is selected from the group consisting of L-lysine, L-threonine, L-tryptophan, L-phenylalanine, L-glutamic acid, and combinations thereof.

It is a further aspect of the invention to provide the production method as described above, wherein the L-amino acid is L-lysine, and the L-amino acid biosynthetic enzyme is selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyl diaminopimelate deacylase, and combinations thereof.

It is a further aspect of the invention to provide the production method as described above, wherein the L-amino acid is L-threonine, and the L-amino acid biosynthetic enzyme is selected from the group consisting of aspartokinase III, aspartate semialdehyde dehydrogenase, aspartokinase I, homoserine kinase, threonine synthase encoded by the thr operon, and combinations thereof.

It is a further aspect of the invention to provide the production method as described above, wherein the L-amino acid is L-glutamic acid, and the L-amino acid biosynthetic enzyme is selected from the group consisting of glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, 6-phosphogluconate dehydratase, 2-keto-3-deoxy-6-phosphogluconate aldolase, and combinations thereof.

It is a further aspect of the invention to provide the production method as described above, wherein the L-amino acid is an aromatic L-amino acid, and the L-amino acid biosynthetic enzyme is selected from the group consisting of 3-deoxy-D-arabinoheptulonate-7-phosphate synthase, 3-dehydroquinate synthase, shikimate dehydratase, shikimate kinase, 5-enolpyruvylshikimate 3-phosphate synthase, chorismate synthase, prephenate dehydratase, chorismate mutase, and combinations thereof.

According to the present invention, a microorganism belonging to the Enterobacteriaceae family, such as *Escherichia* bacteria is provided, which shows high productivity of an L-amino acid such as L-lysine and L-phenylalanine. By using this microorganism, an L-amino acid such as L-lysine and L-phenylalanine can be obtained with high yield.

DESCRIPTION OF THE PREFERRED EMBODIMENTS

<1> Microorganism

Figure 1:
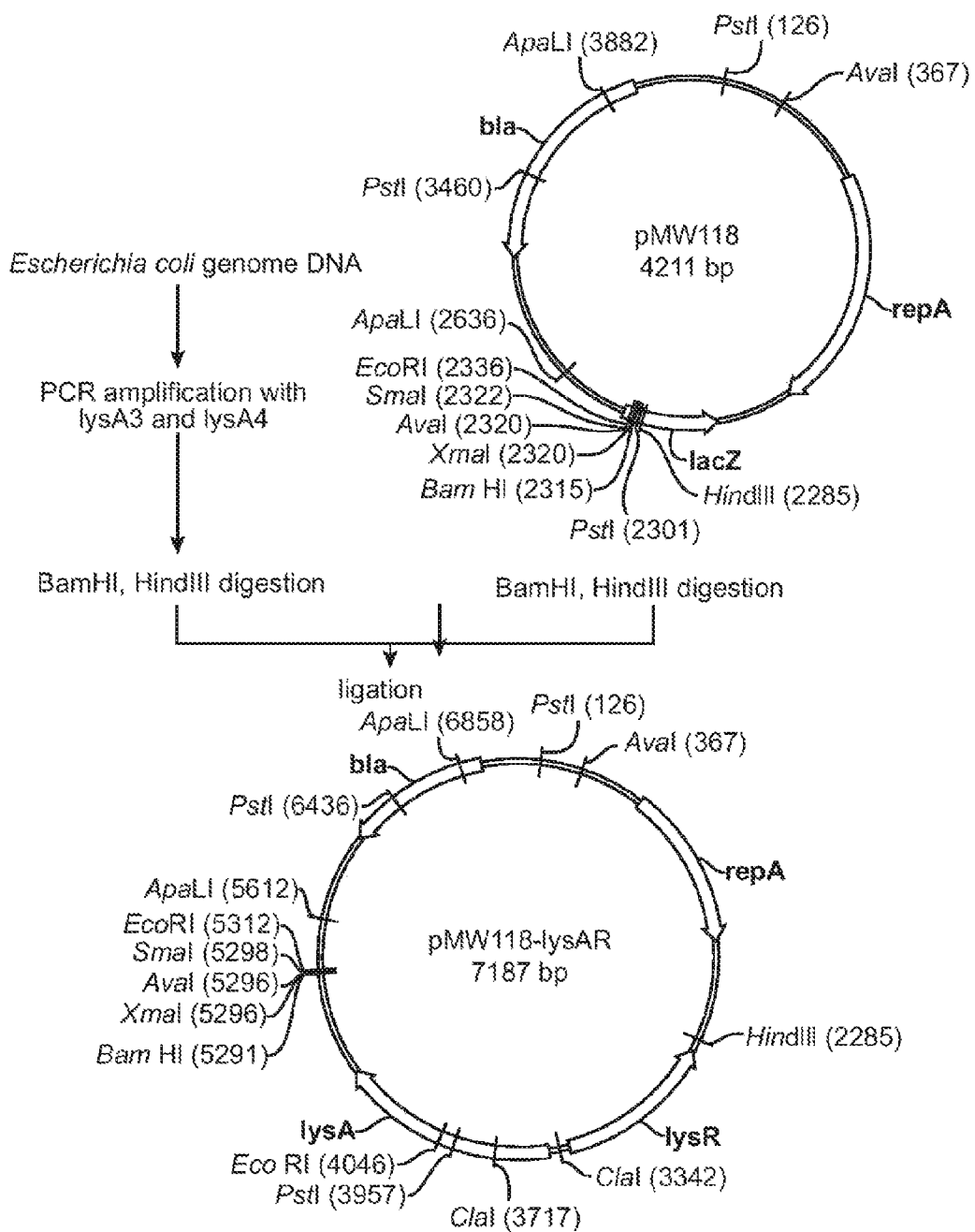
FIG. 1 shows the production process of the pMW-lysAR plasmid containing the lysR gene and the lysA gene.
Figure 2:
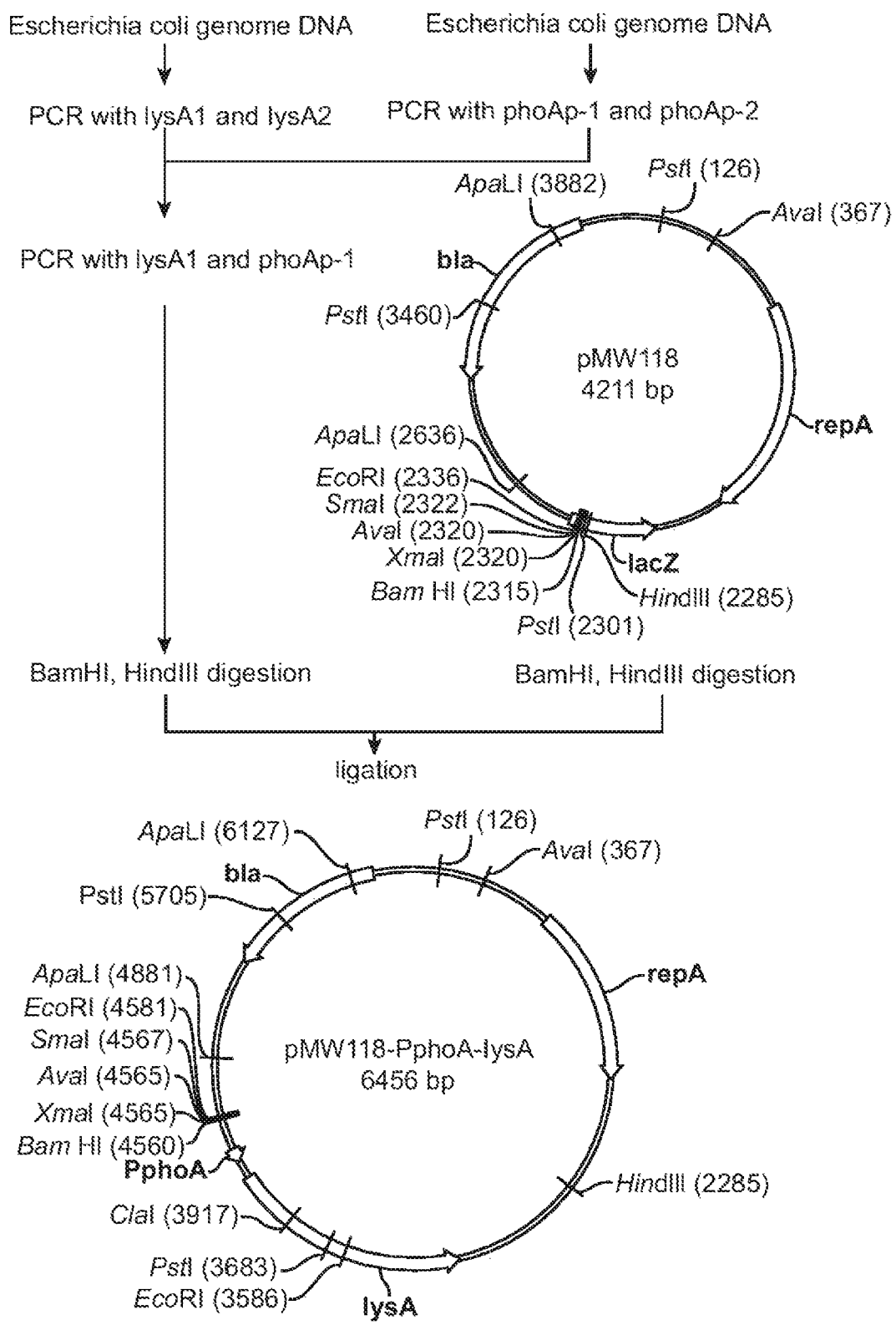
FIG. 2 shows the production process of the pMW-PphoA-lysA plasmid containing the promoter sequence of the phoA gene upstream of the lysA gene.

The microorganism described herein belongs to the Enterobacteriaceae family, and is able to produce an L-amino acid. The microorganism is modified by the introduction of a DNA fragment which includes a pho regulon promoter and a structural gene encoding an L-amino acid biosynthetic enzyme which is ligated downstream of the promoter so that the gene is expressed by the promoter. As a result, the induction of the expression by the promoter increases the activity of the L-amino acid biosynthetic enzyme. The "ability to produce an L-amino acid" means the ability of the microorganism to produce and cause accumulation of the L-amino acid in the medium or the bacterial cells when the microorganism is cultured in the medium. The microorganism of the present invention may be able to produce two or more kinds of L-amino acids. The microorganism may have an inherent ability to produce an L-amino acid, or the microorganism may be modified (see <1-2> below) so that it has an ability to produce the L-amino acid by a mutation method or a recombinant DNA technique.

Although the type of the L-amino acid is not particularly limited, examples include basic amino acids such as L-lysine, L-ornithine, L-arginine, L-histidine and L-citrulline, aliphatic amino acids such as L-isoleucine, L-alanine, L-valine, L-leucine, and L-glycine, amino acids which are hydroxy-monoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, acidic amino acids such as L-glutamic acid, L-asparatic acid, L-glutamine and L-asparagine, and acid amides thereof. Among these, L-lysine, L-phenylalanine, L-tryptophan, L-threonine, and L-glutamic acid are preferred. The microorganism may have the ability to produce two or more kinds of amino acids.

<1-1> DNA Fragment

The DNA fragment described herein includes a pho regulon promoter and a structural gene encoding an L-amino acid biosynthetic enzyme, which is ligated downstream of the promoter so that the gene is expressed by the promoter.

The pho regulon means a gene cluster, expression of which is induced when intracellular phosphorus concentration decreases, and usually means a cluster of genes which are regulated via a pathway for activating transcription factors under the control of the histidine-aspartic acid phosphate relay system of phoB-phoR.

A sensor kinase, PhoR, detects the intracellular phosphorus concentration, induces self-phosphorylation of a histidine residue, and transfers phosphate to a specific aspartic acid residue of the PhoB protein. The PhoB protein is a response regulator and is also a transcription factor. The PhoB protein is activated by this phosphorylation and controls the transcription of many genes.

Examples of the genes in the pho regulon cluster include, for example, pstSCAB, ugpBAEC, ugpQ, bap, phnSTUV, phnCDE, phoE, phoA, and so forth.

Furthermore, the pho regulon promoter promotes expression of the genes of the pho regulon. It usually is present upstream of the gene which is regulated at the transcriptional level by the binary regulation system of phoB-phoR when intracellular phosphorus concentration decreases, and it has a PhoB-binding region. Specific examples include the promoter of genes such as phoA, phoB, phoE, phoH, asr, argP, ugpB, pstS, psiE and phnC. The information on these genes is shown below.

TABLE 1

| Gene | Function | GenBank Accession No. | Literature | Promoter sequence (SEQ ID NO) |
|---|---|---|---|---|
| phoA (psiA, psiF) | Alkaline phosphatase (EC: 3.1.3.1) | NC_000913.2: 400971 ... 402386 | Nucleic Acids Res. 9 (21), 5671-5678 (1981) | 1 2 |
| phoB | Positive response regulator for pho regulon, sensor is PhoR | NC_000913.2: 416366 ... 417055 | Gene 161 (1), 7-10 (1995) | 3 4 |
| phoE | outer membrane pore protein E | Complementary strand of NC_000913.2: 258269 ... 259324 | FEMS Immunol. Med. Microbiol. 16 (2), 77-82 (1996) | 5 6 |

TABLE 1-continued

| Gene | Function | GenBank Accession No. | Literature | Promoter sequence (SEQ ID NO) |
|---|---|---|---|---|
| phoH | PhoB-dependent, ATP-binding pho regulon component | NC_000913.2: 1084215 . . . 1085279 | J Bacteriol. 1993 Mar; 175 (5): 1316-24. | 7<br>8 |
| asr | acid shock protein | NC_000913.2: 1669373 . . . 1669708 | J Bacteriol. 1999 Apr; 181 (7): 2084-93. | 9<br>10 |
| argP (argT) | lysine-, arginine-, ornithine-binding periplasmic protein | Complementary strand of NC_000913.2: 2425031 . . . 2425813 | J Bacteriol. 2004 Jun; 186 (11): 3539-46. | 11<br>12 |
| ugpB | sn-glycerol 3-phosphate transport protein | Complementary strand of NC_000913.2: 3589032 . . . 3590348 | J Bacteriol. 1982 Jun; 150 (3): 1164-71. | 13<br>14 |
| pstS (nmpA, phoR2, phoR2a, phoS, R2pho) | high-affinity phosphate transport protein | Complementary strand of NC_000913.2: 3908508 . . . 3909548 | J Biosci Bioeng. 2000; 90 (6): 688-90. | 15<br>16 |
| psiE (b4030 yjbA) | phosphate-starvation-inducible protein | NC_000913.2: 4238348 . . . 4238758 | J Bacteriol. 2000 Oct; 182 (19): 5596-9. | 17<br>18 |
| phnC | ATP-binding component of phosphonate transport | Complementary strand of NC_000913.2: 4322400 . . . 4323188 | J Bacteriol. 1996 Aug; 178 (15): 4540-7. | 19<br>20 |

SEQ ID NOs of promoter sequences: The numbers on the lower row in each SEQ ID No. column box represent the SEQ ID NOs of the sequences 500 bp upstream of the start codon, and the numbers on the upper row in each SEQ ID NO. column box represent SEQ ID NOs of the promoter sequences registered at GenBank.

Furthermore, the pho regulon promoter sequence preferably has the pho box. The pho box is the region to which phoB binds, and is highly conserved in microorganisms. Specifically, it is conserved at about from 100 to 10 bp upstream of the start codon, and it preferably has the sequence of SEQ ID NO: 21, with the most highly conserved region being CTGTCAT, which is a part of the −35 region (Neidhardt, F. C. et al., *Escherichia coli* and *Salmonella typhimurium*, American Society for Microbiology, Washington D.C., Chapter 87, FIG. 6).

The promoter sequence may contain a mutation which does not affect the promoter's activity of inducing expression when the intracellular phosphorus concentration is decreased. For example, the promoter sequence may have a homology of usually 90% or more, preferably 95% or more, more preferably 97% or more, to the wild-type sequence of the promoter of any of the following genes: phoA, phoB, phoE, phoH, asr, argP, ugpB, pstS, psiE and phnC (SEQ ID NOS: 1 to 20), but maintains the activity of inducing expression when intracellular phosphorus concentration decreases. More preferably, the promoter sequence has a homology of usually 94% or more, preferably 97% or more, more preferably 99% or more, to the sequence of the promoter of any of the following genes: phoA, phoB, phoE, phoH, asr, argP, ugpB, pstS, psiE and phnC (SEQ ID NOS: 1 to 20), and conserves the CTGTCATA(A/T)A(T/A)CTGT(C/A)A(C/T) (SEQ ID NO: 21) or CTGTCAT region in the −35 region in SEQ ID NO: 21.

Homology (identity) of nucleotide sequences can be determined by using, for example, the algorithm BLAST developed by Karlin and Altschul (Pro. Natl. Acad. Sci. USA, 90, 5873 (1993)) or FASTA (Methods Enzymol., 183, 63 (1990)). The programs called BLASTN and BLASTX have been developed on the basis of the algorithm BLAST (refer to www.ncbi.nlm.nih.gov). Homology is usually calculated with these programs by using the default values.

Although the "L-amino acid biosynthetic enzyme" may be any enzyme which metabolically participates in L-amino acid biosynthesis, enzymes which have decreased expression when phosphorus concentration decreases in the second half of the culture are preferred. The second half of the culture mainly means the amino acid production phase, and is distinguished from the cell proliferation phase. The "cell proliferation phase" means the period in which the phosphorus and carbon sources are mainly used for cell growth, for example, the period in which the microorganism is logarithmically increasing, over 3 hours, preferably 6 hours, particularly preferably 10 hours, from the start of the culture. The "second half of the culture" means the period in which the carbon source is mainly used for L-amino acid production, which is a period of 6 hours, preferably 10 hours, particularly preferably 20 hours, before the end of the culture.

The enzyme which is expressed less when the phosphorus concentration decreases in the second half of culture can be confirmed by comparing the enzymatic activity in the second half of the culture (the amino acid production phase) to that in the first half of culture, which is the cell proliferation phase (logarithmic phase). Furthermore, it can also be confirmed by comparing the amounts of mRNAs present in the second half of culture to that in the first half of culture using a DNA macroarray, RT-PCR, or the like.

As for the gene encoding the L-amino acid biosynthetic enzyme, only one kind of gene may be used, or two or more kinds of genes may be used in combination, so long as the gene(s) are effective to produce an L-amino acid. Furthermore, the gene of interest may be an endogenous gene present on the chromosome of *Escherichia coli*, or may be an exogenous gene derived from another microorganism.

Hereafter, the gene encoding an L-amino acid biosynthetic enzyme will be explained in detail.

Examples of the gene encoding an L-lysine biosynthetic enzyme include genes encoding enzymes of the diaminopimelate pathway such as dihydrodipicolinate synthase gene (dapA), aspartokinase gene (lysC), dihydrodipicolinate reductase gene (dapB), diaminopimelate decarboxylase gene (lysA, SEQ ID NO: 28), diaminopimelate dehydrogenase gene (ddh) (International Publication WO96/40934, US 2003-0054506A for all the above), phosphoenolpyruvate carboxylase gene (ppc) (Japanese Patent Laid-open (Kokai, JP-A) No. 60-87788), aspartate aminotransferase gene (aspC) (Japanese Patent Publication (Kokoku, JP-B) No. 6-102028), diaminopimelate epimerase gene (dapF) (JP 2003-135066 A), and aspartate semialdehyde dehydrogenase gene (asd) (International Publication WO01/53459), genes encoding enzymes of the aminoadipate pathway such as homoaconitate hydratase gene (JP 2000-157276 A), and so forth. Examples further include the tetrahydrodipicolinate succinylase gene (dapD) and succinyl-diaminopimelate deacylase gene (dapE). Among these, dapB, lysA, ddh, pepC, aspC, dapF, asd, dapD and dapE are preferred. The entire nucleotide sequence of *Escherichia coli* has already been elucidated (Science, 277, 1453-1474 (1997)), and the gene sequences can be obtained on the basis of the reports of their sequences in the above literature, or their registrations at GenBank.

Examples of the gene encoding an L-glutamic acid biosynthetic enzyme include the L-glutamate dehydrogenase gene (gdh), glutamine synthetase gene (glnA), glutamate synthase gene (ghBD), isocitrate dehydrogenase gene (icd), aconitate hydratase gene (acn), citrate synthase gene (gltA), pyruvate dehydrogenase gene (pdh), and so forth (U.S. Pat. Nos. 6,197,559, 6,331,419, European Patent No. 0999282). Examples further include the phosphoenolpyruvate carboxylase gene (pepC), pyruvate carboxylase gene (pc), pyruvate kinase genes (pykA, pykF), phosphoenolpyruvate synthase gene (pps), 6-phosphogluconate dehydratase gene (edd), 2-keto-3-deoxy-6-phosphogluconate aldolase gene (eda) (European patent No. 1352966, U.S. Pat. Nos. 7,037,690), and so forth.

Examples of the gene encoding an L-threonine biosynthetic enzyme include the aspartokinase III gene (lysC), aspartate semialdehyde dehydrogenase gene (asd), aspartokinase I gene (thrA), homoserine kinase gene (thrB), and threonine synthase gene (thrC), which are encoded by the thr operon. Furthermore, the biosynthesis of L-threonine overlaps with that of L-lysine, and therefore the gene encoding an L-lysine biosynthetic enzyme may also be amplified.

Enzymatic activity of the L-threonine biosynthetic enzyme is suppressed by L-threonine. Therefore, it is desirable to use a gene which has been modified so that it is not subject to feedback inhibition by L-threonine (refer to International Publication WO02/26993, Biotechnology Letters, vol. 24, No. 21, November 2002, International Publication WO2005/049808).

L-tryptophan, L-phenylalanine, and L-tyrosine are aromatic amino acids, and they have common biosynthesis systems. Examples of the gene encoding a biosynthetic enzyme of an aromatic amino acid include the 3-deoxy-D-arabino-heptulonate 7-phosphate synthase gene (aroF, aroG, SEQ ID NO: 36), 3-dehydroquinate synthase gene (aroB), shikimate dehydratase gene, shikimate kinase gene (aroL, SEQ ID NO: 38), 5-enolpyruvylshikimate 3-phosphate synthase gene (aroA), and chorismate synthase gene (aroC) (EP 763127 A, WO9533843).

Furthermore, since 3-deoxy-D-arabinoheptulonate 7-phosphate synthase (aroF, aroG) is subject to feedback inhibition by an aromatic amino acid, it may be modified so that it is not subject to feedback inhibition. For example, aroF may be modified by replacing the 147-th L-asparatic acid or 181-st L-serine residue as counted from the N terminus with another amino acid residue. The aroG may be modified by replacing either of the 146th L-asparatic acid, 147th L-methionine, 150th L-proline, or 202nd L-alanine with another amino acid, or replacing both of the 157th L-methionine and 219th L-alanine with another amino acid (EP 0488424, U.S. Pat. No. 5,618,716).

Examples of the gene encoding an L-tryptophan biosynthetic enzyme include the anthranilate synthetase gene (trpE), phosphoglycerate dehydrogenase gene (serA), and tryptophan synthase gene (trpAB). However, it is more effective to use a variant gene obtained by modifying the phosphoglycerate dehydrogenase gene (serA) so that the enzyme is not subject to feedback inhibition (International Publication WO93/12235). Furthermore, a recombinant DNA containing the tryptophan operon may also be used as the structural gene. Specific examples include a tryptophan operon which includes a gene encoding desensitized anthranilate synthetase (JP 57-71397 A, JP 62-244382 A, U.S. Pat. No. 4,371,614). Furthermore, by enhancing expression of the gene encoding tryptophan synthase (trpBA) on the tryptophan operon, the L-tryptophan-producing ability can be improved or imparted. Tryptophan synthase has α- and β-subunits encoded by trpA and trpB, respectively (U.S. Pat. No. 4,371,614).

Examples of the genes encoding L-phenylalanine or L-tyrosine biosynthetic enzymes include the prephenate dehydratase gene (tyrAlpheA, U.S. Pat. No. 4,371,614, Japanese Patent No. 3060688), tyrosine aminotransferase gene (tyrB, U.S. Pat. No. 5,091,314), and chorismate mutase gene (pheA, SEQ ID NO: 40). It is known that prephenate dehydratase and chorismate mutase are subject to feedback inhibition by phenylalanine, and therefore it is preferable to introduce a mutation which eliminates or reduces the feedback inhibition by phenylalanine. For example, it is preferable to use prephenate dehydratase or chorismate mutase of SEQ ID NO: 40 in which the 330th serine residue is replaced with another amino acid residue, desirably a proline residue, or the 226th tryptophan residue is replaced with another amino acid residue, and the 338th tryptophan residue is replaced with another amino acid residue, desirably an arginine or glycine residue (Japanese Patent No. 3060668, JP 1-235597 A). Furthermore, by improving the expression of the gene which regulates the uptake of a by-product into cells such as the L-tryptophan uptake genes, tnaB and mtr, and the L-tyrosine uptake gene, tyrP, a strain which efficiently produces L-phenylalanine can be obtained (EP 1484410).

Examples of the gene encoding an L-arginine biosynthetic enzyme include one or more of the following genes: the N-acetylglutamate synthase gene (argA), N-acetylglutamyl phosphate reductase gene (argC), ornithine acetyltransferase gene (argJ), N-acetylglutamate kinase gene (argB), acetylornithine transaminase gene (argD), acetylornithine deacetylase gene (argE), ornithine carbamoyltransferase gene (argF), argininosuccinate synthase gene (argG), argininosuccinate lyase gene (argH) and carbamoyl phosphate synthase gene (carAB) (JP 63-79597 A). It is more preferable to use a variant type N-acetylglutamate synthase gene (argA) in which the 15th to 19th amino acids in the wild-type sequence are replaced and the feedback inhibition by L-arginine is eliminated (EP 1170361 A).

L-leucine, L-valine, and L-isoleucine are branched chain amino acids, and they have common biosynthesis systems. Examples of the gene encoding an enzyme common to the branched chain amino acid biosynthesis systems include the pyruvate dehydrogenase gene (aceE) (International Publication WO03/076635).

Examples of the gene encoding an L-valine or L-isoleucine biosynthetic enzyme include the acetohydroxy acid synthase gene (ilvGM), branched chain amino acid aminotransferase gene (ilvE), dihydroxy acid dehydratase gene (ilvD), and threonine dehydratase gene (ilvA). Among these, ilvGMEDA constitutes an operon, and it may be used as the operon, or the individual genes may be used independently. Since the ilvGMEDA operon is attenuated by L-valine and/or L-isoleucine, and/or L-leucine, the region required for the attenuation is preferably removed or mutated in order to eliminate the attenuation (U.S. Pat. No. 5,998,178).

Furthermore, L-threonine is a precursor in the production of L-isoleucine. Therefore, in order to enhance the ability to produce L-isoleucine, it is preferable to increase the supply of L-threonine, i.e., to enhance the biosynthesis system of L-threonine. Accordingly, the aforementioned L-threonine biosynthesis system may be enhanced, along with enhancing a gene encoding a biosynthetic enzyme specific to L-isoleucine biosynthesis.

Examples of the gene encoding an L-leucine biosynthetic enzyme include the 2-isopropyl malate synthase gene (leuA), 2-isopropyl malate isomerase gene (leuD), 2-isopropyl malate dehydrogenase gene (leuB), and a branched chain amino acid aminotransferase gene (ilvE, Canadian Patent No. 1341352). Since 2-isopropyl malate synthase suffers from feedback inhibition by L-leucine, it is preferable to use leuA with the feedback inhibition of isopropyl malate synthase by L-leucine being desensitized (U.S. Pat. No. 6,403,342).

Examples of the gene encoding an L-histidine biosynthetic enzyme include the ATP phosphoribosyl transferase gene (hisG), phosphoribosyl AMP cyclohydrolase gene (hisI), phosphoribosyl ATP pyrophosphohydrolase gene (hisIE), phosphoribosylformimino-5-aminoimidazole carboxamide ribotide isomerase gene (hisA), amidotransferase gene (hisH), histidinol phosphate aminotransferase gene (hisC), histidinol phosphatase gene (hisB), histidinol dehydrogenase gene (hisD), and so forth (U.S. Pat. No. 4,388,405).

Examples of the gene encoding an L-cysteine biosynthetic enzyme include the phosphoglycerate dehydrogenase gene (serA), serine acetyltransferase gene (cysE, International Publication WO2005/007841), and cysteine synthase gene (cysK, International Publication WO03/06666).

The DNA fragment of the present invention can be obtained by, for example, the following methods.

First, a pho regulon promoter sequence and an L-amino acid biosynthetic gene are separately cloned by PCR or the like. Oligonucleotides used for PCR are designed by referring to publicly available databases. Furthermore, if a restriction enzyme site is ligated to the N termini of oligonucleotides for PCR, two DNAs can be easily ligated.

The plasmid used for the cloning of the gene may be any plasmid, so long as it is autonomously replicable in Enterobacteriaceae bacteria. Specific examples include pBR322, pTWV228 (Takara Bio), pMW119 (Nippon Gene), pUC19, pSTV29 (Takara Bio), RSF1010 (Gene, vol. 75 (2), p 271-288, 1989), and so forth. Besides these, phage DNA vectors can also be used.

The method for introducing the DNA fragment into a microorganism belonging to the Enterobacteriaceae family will be explained below.

The DNA fragment can be introduced into a host, for example, as follows. That is, the DNA fragment can be ligated to a vector which functions in the host microorganism, preferably a multi-copy vector, to prepare a recombinant DNA, and the host can be transformed with the recombinant DNA to introduce the DNA fragment into the host.

In order to ligate the gene of interest (a gene expressed under the control of the pho regulon promoter) to the aforementioned vector to prepare a recombinant DNA, the vector is digested with the restriction enzyme which corresponds to the end of the DNA fragment containing the gene of interest. The ligation is usually performed with a ligase such as T4 DNA ligase. When there are more than one gene of interest, the may be carried on separate vectors, or they may be carried on the same vector. As the methods for digestion and ligation of DNA as well as preparation of chromosomal DNA, PCR, preparation of plasmid DNA, transformation, design of oligonucleotides used as primers, and so forth, methods well known to those skilled in the art can be used. Such methods are described in Sambrook, J., Fritsch, E. F. and Maniatis, T., "Molecular Cloning A Laboratory Manual and Second Edition", Cold Spring Harbor Laboratory Press (1989), and so forth. In order to introduce a recombinant DNA prepared as described above into a microorganism, any method may be used, so long as sufficient transformation efficiency is obtained. Examples of the method include, for example, electroporation (Canadian Journal of Microbiology, 43.197 (1997)).

Furthermore, the DNA fragment can also be obtained by ligating the pho regulon promoter at a position upstream of the gene of interest. The pho regulon promoter can be introduced at a position upstream of the gene by gene substitution based on homologous recombination described in Sambrook, J., and Russell, D. W., Molecular Cloning A Laboratory Manual/Third Edition, New York: Cold Spring Harbor Laboratory Press (2001), and so forth. The position upstream of the gene where the pho regulon promoter is inserted is not particularly limited, so long as the promoter is inserted at such a position that the activity of the enzyme encoded by the gene is not reduced. However, the promoter is desirably inserted at a position upstream of the SD sequence (Shine-Dalgalno sequence), and the promoter may replace the gene's own promoter.

The gene's own whole promoter sequence may be replaced with a pho regulon promoter, for example, such as phoA, phoB, phoE, phoH, asr, argP, ugpB, pstS, psiE and phnC. Furthermore, the pho box may be introduced into a region upstream of the gene, specifically, the sequence of SEQ ID NO: 21 may be introduced, and more specifically, the CTGTCAT sequence may be introduced into the −35 region of the gene. (Neidhardt, F. C. et al., *Escherichia coli* and *Salmonella Typhimurium*, American Society for Microbiology, Washington D.C., Chapter 87, FIG. 6)

Furthermore, the DNA fragment can also be introduced into the chromosomal DNA of the microorganism. Specifically, homologous recombination can be employed using a sequence present in multiple copies on the chromosomal DNA or a locus on the chromosome which is not required for the production of the objective substance. Such site-specific mutagenesis by gene substitution utilizing homologous recombination has already been established, and examples of this method include using a linear DNA or a plasmid containing a temperature sensitive replication origin (U.S. Pat. No. 6,303,383, JP 05-007491 A), and so forth. Sequences present in multiple copies on chromosomal DNA include repetitive DNA and inverted repeats present at the end of a transposable element. Alternatively, as disclosed in JP 2-109985 A, it is also possible to introduce the gene into a transposon, and allow it to introduce multiple copies of the gene into the chromosomal DNA.

Furthermore, the DNA fragment can also be introduced by the method called "Red-driven integration" developed first by Datsenko and Wanner (Proc. Natl. Acad. Sci. USA, 2000, vol. 97, No. 12, pp. 6640-6645). According to the "Red-driven integration" method, it is possible to insert the DNA fragment into the chromosome in one step by using the PCR product obtained with synthetic oligonucleotides designed so as to have a part of the gene on the 5' side, and a part of an antibiotic resistance gene on the 3' side.

Although it is sufficient that one copy of the DNA fragment is introduced into the microorganism, it is preferable to further enhance expression by increasing the copy number of the DNA fragment. For example, the copy number in the cell is increased to 2 or more, preferably 3 or more, more preferably 4 or more.

The copy number can be increased by using a multi-copy vector carrying the gene. Examples of vectors which are autonomously replicable in Enterobacteriaceae bacteria include pUC19, pUC18, pHSG299, pHSG399, pHSG398, pACYC184 (pHSG and pACYC are available from Takara Bio), RSF1010 (Gene, vol. 75 (2), pp. 271-288, 1989), pBR322, pMW219, pMW119 (pMW series plasmids are available from Nippon Gene), pSTV28, pSTV29 (Takara Bio), and so forth (Microbiological Review, 60 (3), 512-538 (1996), U.S. Pat. No. 5,538,873). Besides these, lambda phage DNA vectors and Mu phage vectors can also be used (EP 0332448)

The copy number can also be increased by introducing multiple copies of the DNA fragment into the chromosomal DNA of the microorganism. In order to introduce multiple copies of the gene into the chromosomal DNA of the microorganism, homologous recombination is carried out by using a target sequence which is present in multiple copies on the chromosomal DNA. Such site-specific mutagenesis by gene substitution utilizing homologous recombination has already been established, and examples of the method include using a linear DNA or a plasmid containing a temperature-sensitive replication origin (U.S. Pat. No. 6,303,383, JP 05-007491 A), and so forth. Sequences which are present in multiple copies on the chromosomal DNA include repetitive DNA and inverted repeats present at the end of a transposable element. Alternatively, as disclosed in JP 2-109985 A, it is also possible to incorporate the gene into a transposon, and allow it to introduce multiple copies of the genes into the chromosomal DNA. As a result of the increase of the copy number of the gene in the transformant attained by any of these methods, the activity of the enzyme of the L-lysine biosynthesis system is increased.

Besides the gene amplification described above, expression of the gene can also be enhanced by replacing the promoter of the L-amino acid biosynthesis system gene upstream or downstream of the pho regulon promoter with a more potent promoter (refer to JP 1-215280 A). For example, the lac promoter, trp promoter, trc promoter, tac promoter, $P_R$ promoter and $P_L$ promoter of lambda phage, tet promoter, and so forth are known as potent promoters. By replacing these promoters, expression of the gene is enhanced, and the enzymatic activity is amplified. To evaluate the potency of promoters and see examples of potent promoters, the paper of Goldstein et al. is referenced (Prokaryotic promoters in biotechnology, Biotechnol. Annu. Rev., 1995, 1, 105-128) and so forth. It is desirable that these promoters are ligated to a region upstream or downstream of the pho regulon promoter, and the expression is regulated by both the pho regulon promoter and the potent promoter.

Moreover, as disclosed in International Publication WO00/18935, it is also possible to substitute several nucleotides in the promoter which are specific to the L-amino acid biosynthesis enzyme gene, which results in a more potent promoter for the gene. Furthermore, it is known that replacing several nucleotides in the spacer region between the ribosome binding site (RBS) and the start codon, especially in the region immediately upstream of the start codon, significantly effects the translation efficiency of the mRNA. Expression control regions of the gene can be determined by using a promoter searching vector, gene analysis software such as GENETYX, or the like. The expression control sequence can be substituted, for example, in the same manner as that of the aforementioned gene substitution using a temperature-sensitive plasmid.

Moreover, the nucleotide sequence which encodes the L-amino acid biosynthetic enzyme may differ among the species or strains of *Escherichia coli*, and therefore the gene may be a mutant, or an artificially modified gene, encoding a protein which includes substitution, deletion, insertion, addition or the like of one or several amino acid residues at one or more positions, so long as the activity encoded by the gene is maintained. Although the number of the "several" amino acid residues may differ depending on the positions in the three-dimensional structure or types of amino acid residues of the protein, specifically, it may be 1 to 20, preferably 1 to 10, more preferably 1 to 5. The substitutions, deletions, insertions or additions of amino acid residues as mentioned above are conservative mutations which maintain the enzymatic activity. Typical examples of conservative mutations are conservative substitutions, such as substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Thr for Trp, substitution of His, Phe or Trp for Tyr, and substitution of Met, Ile or Leu for Val.

Furthermore, the gene encoding the L-amino acid biosynthetic enzyme may be a DNA which can hybridize with the nucleotide sequence of the gene or a probe which can be prepared from the sequence under stringent conditions, so long as the activity of the encoded enzyme is maintained. The "stringent conditions" are those under which a so-called specific hybrid is formed, and a non-specific hybrid is not formed. Examples of the stringent conditions include those under which highly homologous DNAs hybridize to each other, for example, DNAs not less than 70% homologous, hybridize to each other, and DNAs less homologous than the above do not hybridize to each other, and washing once or preferably 2 or 3 times at a salt concentration and temperature corresponding to washing conditions typical Southern hybridization, i.e., 1×SSC, 0.1% SDS at 60° C., preferably 0.1×SSC, 0.1% SDS at 60° C., more preferably 0.1×SSC, 0.1% SDS at 68° C. Although length of the probe is suitably chosen according to the conditions of the hybridization, it is usually 100 bp to 1 kbp.

Furthermore, the gene also may encode a protein having a homology of 80% or more, preferably 90% or more, more preferably 95% or more, particularly preferably 97% or more, to the amino acid sequence of the wild-type strain and having the activity of the L-amino acid biosynthetic enzyme. The calculation method of homology is the same as that described for the promoter sequences. Moreover, since the degeneracy of gene can be different depending on the host, the gene may have codons which are replaced with codons which are more compatible in the chosen host. The gene may also be extended or shortened so as to extend or shorten the protein on the N-terminus side or the C-terminus side, so long as it encodes a protein having the activity of an L-amino acid biosynthetic enzyme. The length of the extension or shortening is, for example, 50 or less, preferably 20 or less, more preferably 10 or less, particularly preferably 5 or less, in terms of the number of amino acid residues. More specifically, the amino acid sequence may be extended on either the N-terminus side or C-terminus side 50 to 5 amino acid residues, or it ma be shortened by 50 to 5 amino acid residues on the N-terminus side or C-terminus side.

<1-2> Parent Strain

Microorganisms belonging to the family Enterobacteriaceae can be used as parent strains, and typical examples include *Escherichia* bacteria and *Pantoea* bacteria. Other examples of microorganisms belonging to the family Enterobacteriaceae include γ-proteobacteria belonging to the family Enterobacteriaceae such as those of the genus *Enterobacter, Klebsiella, Serratia, Erwinia, Salmonella, Morganella* or the like.

*Escherichia* bacteria mentioned in the work of Neidhardt et al. (Backmann B. J., 1996, Derivations and Genotypes of some mutant derivatives of *Escherichia coli* K-12, pp. 2460-2488, Table 1. In F. D. Neidhardt (ed.), *Escherichia coli* and *Salmonella* Cellular and Molecular Biology/Second Edition, American Society for Microbiology Press, Washington, D.C.), such as *Escherichia coli*, can be utilized. Examples of wild-type strains of *Escherichia coli* include, for example, the K12 strain and derivatives thereof, *Escherichia coli* MG1655 strain (ATCC No. 47076), W3110 strain (ATCC No. 27325), and so forth. These strains may be obtained from, for example, the American Type Culture Collection (ATCC, Address: P.O. Box 1549, Manassas, Va. 20108, United States of America).

Examples of the *Enterobacter* bacteria include *Enterobacter agglomerans, Enterobacter aerogenes*, and so forth. Examples of the *Pantoea* bacteria include *Pantoea ananatis*. In recent years, *Enterobacter agglomerans* was re-classified into *Pantoea* agglomerans, *Pantoea ananatis, Pantoea stewartii*, or the like on the basis of nucleotide sequence analysis of the 16S rRNA, etc. The microorganism may belong to either the genus *Enterobacter* or *Pantoea*, so long as it is classified as the family Enterobacteriaceae. When a *Pantoea ananatis* strain is bred by a genetic engineering technique, *Pantoea ananatis* AJ13355 strain (FERM BP-6614), AJ13356 strain (FERM BP-6615), AJ13601 strain (FERM BP-7207), and derivatives thereof can be used. These strains were identified as *Enterobacter agglomerans* when they were isolated, and deposited as *Enterobacter agglomerans*. However, they were recently re-classified as *Pantoea ananatis* on the basis of nucleotide sequence analysis of the 16S rRNA and so forth as described above.

In order to impart the ability to produce an L-amino acid, the methods conventionally employed for breeding of *Escherichia* bacteria and so forth, such as the breeding of auxotrophic mutant strains, analogue resistant strains, and metabolic regulation variant strains, as well as the creation of recombinant strains in which expression of an L-amino acid biosynthetic enzyme is increased (refer to Amino Acid Fermentation, pp. 77-100, Japan Scientific Societies Press, first edition was issued on May 30, 1986) can be applied. In the breeding of an L-amino acid producing bacterium, the characteristics such as auxotrophy, analogue resistance, and metabolic regulation mutations may be imparted independently, or two or more of them may be imparted together. One or more L-amino acid biosynthetic enzymes may have increased expression. Furthermore, the impartation of characteristics such as auxotrophy, analogue resistance, and metabolic regulation mutations, and the increase of the activity of the biosynthetic enzyme may be used in combination.

These various strains having the above-described characteristics may be obtained by subjecting a parent strain or wild-type strain to a typical mutatgenesis treatment, i.e., radiating with X-ray or ultraviolet light, or treating with a mutatgenesis agent such as N-methyl-N'-nitro-N-nitrosoguanidine (NTG) and ethyl methanesulfonate (EMS). Then, strains exhibiting auxotrophy, analogue resistance, or a metabolic regulation mutation, and which are able to produce an L-amino acid can be selected from the variant strains.

L-threonine-Producing Bacteria

Examples of parent strains for deriving the L-threonine-producing bacteria of the present invention include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A) and the like.

The strain TDH-6 is deficient in the thrC gene, as well as being sucrose-assimilative, and the HvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which is substantially desensitized to feedback inhibition by threonine. The strain B-3996 was deposited on Nov. 19, 1987 in the All-Union Scientific Center of Antibiotics (Nagatinskaya Street 3-A, 117105 Moscow, Russia) under the accession number RIA 1867. The strain was also deposited in the Russian National Collection of Industrial Microorganisms (VKPM) (1 Dorozhny proezd., 1 Moscow 117545, Russia) on Apr. 7, 1987 under the accession number VKPM B-3996.

*E. coli* VKPM B-5318 (EP 0593792B) may also be used to derive L-threonine-producing bacteria. The strain B-5318 is prototrophic with regard to isoleucine, and the temperature-sensitive lambda-phage C1 repressor and PR promoter replaces the regulatory region of the threonine operon in the pVIC40 plasmid. The strain VKPM B-5318 was deposited in the Russian National Collection of Industrial Microorganisms (VKPM) on May 3, 1990 under accession number of VKPM B-5318.

Preferably, the bacterium is additionally modified to enhance expression of one or more of the following genes: the mutant thrA gene which encodes aspartokinase homoserine dehydrogenase I resistant to feedback inhibition by threonine, the thrB gene which encodes homoserine kinase, the thrC gene which encodes threonine synthase, the rhtA gene which encodes a putative transmembrane protein, the asd gene which encodes aspartate-(3-semialdehyde dehydrogenase, and the aspC gene which encodes aspartate aminotransferase (aspartate transaminase).

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC 000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC 000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription can be removed (WO2005/049808, WO2003/097839).

The mutant thrA gene which encodes aspartokinase homoserine dehydrogenase I resistant to feedback inhibition by threonine, as well as, the thrB and thrC genes can be obtained as one operon from the well-known plasmid pVIC40, which is present in the threonine-producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet, 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC 000913.1, gi:16128895), and can be obtained by PCR. The aspC genes from other microorganisms can be obtained in a similar manner.

L-lysine-Producing Bacteria

Examples of L-lysine-producing bacteria belonging to the genus *Escherichia* include mutants having resistance to L-lysine analogues. The L-lysine analogue inhibits the growth of bacteria belonging to the genus *Escherichia*, but this inhibition is fully or partially desensitized when L-lysine is present in the medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The WC1-96 strain is an L-lysine-producing bacterium of *Escherichia coli*. This bacterial strain was bred by conferring AEC resistance to the W3110 strain, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria also include strains in which expression of one or more genes encoding L-lysine biosynthetic enzymes are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains which can be used to derive L-lysine-producing bacteria also include strains with decreased or no activity of an enzyme that catalyzes a reaction which branches off of the biosynthetic pathway of L-lysine. Examples of such enzymes include homoserine dehydrogenase, lysine decarboxylase (U.S. Pat. No. 5,827,698), and the malic enzyme (WO2005/010175).

L-cysteine-Producing Bacteria

Examples of parent strains which can be used to derive L-cysteine-producing bacteria include, but are not limited to, strains belonging to the genus *Escherichia*, such as *E. coli* JM15 which is transformed with different cysE alleles encoding feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571 A2); *E. coli* W3110 with increased activity of a positive transcriptional regulator for cysteine regulon encoded by the cysB gene (WO 127307A1), and the like.

L-leucine-Producing Bacteria

Examples of parent strains which can be used to derive L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the genetic engineering method described in WO96/06926; *E. coli* H-9068 (JP 8-70879 A), and the like.

The bacterium may be improved by enhancing the expression of one or more genes involved in L-leucine biosynthesis.

Examples include genes of the leuABCD operon, which are preferably a mutant leuA gene encoding isopropylmalate synthase free from feedback inhibition by L-leucine (U.S. Pat. No. 6,403,342). In addition, the bacterium may be improved by enhancing the expression of one or more genes encoding proteins which excrete L-amino acid from the bacterial cell. Examples of such genes include the b2682 and b2683 genes (ygaZH genes) (EP 1239041 A2).

L-histidine-Producing Bacteria

Examples of parent strains which can be used to derive L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B-12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP 1085087); *E. coli* AI80/pFM201 (U.S. Pat. No. 6,258,554), and the like.

Examples of parent strains which can be used to derive L-histidine-producing bacteria also include strains in which expression of one or more genes encoding L-histidine biosynthetic enzymes are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore the L-histidine-producing ability can also be efficiently enhanced by introducing a mutation which confers resistance to the feedback inhibition into ATP phosphoribosyltransferase (Russian Patent Nos. 2003677 and 2119536).

Specific examples of strains having L-histidine-producing ability include *E. coli* FERM-P 5038 and 5048, into which a vector carrying a DNA encoding an L-histidine-biosynthetic enzyme (JP 56-005099 A) has been introduced, *E. coli* strains introduced with rht, a gene for an amino acid-export (EP 1016710A), *E. coli* 80 strain imparted with sulfaguanidine, DL-1,2,4-triazole-3-alanine, and streptomycin-resistance (VKPM B-7270, Russian Patent No. 2119536), and so forth.

L-glutamic Acid-Producing Bacteria

Examples of parent strains which can be used to derive L-glutamic acid-producing bacteria include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in the thrC and ilvA genes (U.S. Pat. No. 4,278,765). A wild-type allele of the thrC gene was transferred by general transduction using a bacteriophage P1 grown on the wild-type *E. coli* strain K12 (VKPM B-7). As a result, the L-isoleucine auxotrophic strain VL334thrC$^+$ (VKPM B-8961), which is able to produce L-glutamic acid, was obtained.

Examples of parent strains which can be used to derive L-glutamic acid-producing bacteria include, but are not limited to, strains in which expression of one or more genes encoding an L-glutamic acid biosynthetic enzyme are enhanced. Examples of such genes include genes encoding glutamate dehydrogenase (gdh), glutamine synthetase (glnA), glutamate synthetase (gltAB), isocitrate dehydrogenase (icd), aconitate hydratase (acn), citrate synthase (gltA), phosphoenolpyruvate carboxylase (pepC), pyruvate carboxylase (pyc), pyruvate dehydrogenase (pdh), pyruvate kinase (pykA,pykF), phosphoenolpyruvate synthase (pps), enolase (eno), phosphoglyceromutase (pgm), phosphoglycerate kinase (pgk), glyceraldehyde-3-phophate dehydrogenase (gap), triose phosphate isomerase (tpi), fructose bisphosphate aldolase (fbp), phosphofructokinase (pfk), and glucose phosphate isomerase (pgi).

Examples of strains which have been modified so that expression of the citrate synthetase gene, the phosphoenolpyruvate carboxylase gene, and/or the glutamate dehydrogenase gene is/are enhanced include those disclosed in EP 1078989 A, EP 955368 A, and EP 952221A.

Examples of parent strains which can be used to derive L-glutamic acid-producing bacteria also include strains having decreased or no activity of an enzyme that catalyzes synthesis of a compound other than L-glutamic acid via a branch of the L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB) (the terms in parenthesis are the names of genes encoding the enzyme). Bacteria belonging to the genus *Escherichia* deficient in α-ketoglutarate dehydrogenase activity or having reduced α-ketoglutarate dehydrogenase activity and methods for obtaining them are described in U.S. Pat. Nos. 5,378,616 and 5,573,945.

Specifically, these strains include the following:
*E. coli* W3110sucA::Km$^R$
*E. coli* AJ12624 (FERM BP-3853)
*E. coli* AJ12628 (FERM BP-3854)
*E. coli* AJ12949 (FERM BP-4881)

*E. coli* W3110sucA::Km$^R$ is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacteria include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid-decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as the result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of the 16S rRNA and so forth. Although AJ13356 was deposited at the aforementioned depository as *Enterobacter agglomerans*, for the purposes of this specification, they are described as *Pantoea ananatis*.

L-phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB] (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, an L-phenylalanine-producing bacterium MG1655ΔtyrAΔtyrR, PL-yddG belonging to the genus *Escherichia* with an enhanced activity of the protein encoded by the yedA gene or the yddG gene may also be used (U.S. application publications 2003/0148473 A1 (WO 03/044192) and 2003/0157667 A1).

L-tryptophan-Producing Bacteria

Examples of parent strains which can be used to derive L-tryptophan-producing bacteria include, but are not limited to, strains belonging to the genus *Escherichia*, such as *E. coli* JP4735/pMU3028 (DSM10122) and JP6015/pMU91 (DSM10123), which are deficient in the tryptophanyl-tRNA synthetase encoded by the mutant trpS gene (U.S. Pat. No. 5,756,345); *E. coli* SV 164 (pGH5) having the serA allele encoding phosphoglycerate dehydrogenase free from feedback inhibition by serine and the trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP(NRRL B-12264), which are deficient in the enzyme tryptophanase (U.S. Pat. No. 4,371,614); *E. coli* AGX17/pGX50,pACKG4-pps in which a phosphoenolpyruvate-producing ability is enhanced (WO9708333, U.S. Pat. No. 6,319,696), and the like may be used.

L-tryptophan-producing bacteria belonging to the genus *Escherichia* with enhanced activity of the identified protein encoded by the yedA gene or the yddG gene may also be used (U.S. application publications 2003/0148473 A1 and 2003/0157667 A1).

Examples of parent strains which can be used to derive L-tryptophan-producing bacteria also include strains in which one or more activities of the enzymes anthranilate synthase, phosphoglycerate dehydrogenase (serA), and tryptophan synthase (trpAB) are enhanced. The anthranilate synthase and phosphoglycerate dehydrogenase are both subject to feedback inhibition by L-tryptophan and L-serine, so a mutation desensitizing the feedback inhibition may be introduced into these enzymes. Specific examples of strains having such a mutation include a *E. coli* SV164 which harbors desensitized anthranilate synthase, and a transformant strain obtained by introducing into *E. coli* SV164 the plasmid pGH5 (WO 94/08031), which contains a mutant serA gene encoding feedback-desensitized phosphoglycerate dehydrogenase.

Examples of parent strains which can be used to derive L-tryptophan-producing bacteria also include strains into which the tryptophan operon which contains the gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of the gene which encodes tryptophan synthase, among the tryptophan operons (trpBA). The tryptophan synthase is made up of α and β subunits which are encoded by the trpA and trpB genes, respectively. In addition, L-tryptophan-producing ability may be improved by enhancing expression of the isocitrate lyase-malate synthase operon (WO2005/103275).

L-proline-Producing Bacteria

Examples of parent strains which can be used to derive L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433).

The bacterium may be improved by enhancing the expression of one or more genes involved in L-proline biosynthesis. Examples of such genes for L-proline producing bacteria which are preferred include the proB gene encoding glutamate kinase of which feedback inhibition by L-proline is desensitized (DE Patent 3127361). In addition, the bacterium of the present invention may be improved by enhancing the expression of one or more genes encoding proteins excreting L-amino acid from bacterial cell. Such genes are exemplified by the b2682 and b2683 genes (ygaZH genes) (EP 1239041 A2).

Examples of bacteria belonging to the genus *Escherichia* which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami winter symposium, 1983, p. 34), and the like.

L-arginine-Producing Bacteria

Examples of parent strains which can be used to derive L-arginine-producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP 1170358A1), an arginine-producing strain into which argA gene encoding N-acetylglutamate synthetase is introduced therein (EP 1170361A1), and the like.

Examples of parent strains which can be used to derive L-arginine producing bacteria also include strains in which expression of one or more genes encoding L-arginine biosynthetic enzymes are enhanced. Examples include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-valine-Producing Bacteria

Examples of parent strains which can be used to derive L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine. Furthermore, the ilvA gene in the operon is desirably disrupted so that threonine deaminase activity is decreased.

Examples of parent strains which can be used to derive L-valine-producing bacteria include mutants having a mutation of amino-acyl t-RNA synthetase (U.S. Pat. No. 5,658, 766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (1 Dorozhny proezd., 1 Moscow 117545, Russia) on Jun. 24, 1988 under accession number VKPM B-4411.

Furthermore, mutants requiring lipoic acid for growth and/or lacking $H^+$-ATPase can also be used as parent strains (WO96/06926).

L-isoleucine-Producing Bacteria

Examples of parent strain which can be used to derive L-isoleucine producing bacteria include, but are not limited to, mutants having resistance to 6-dimethylaminopurine (JP 5-304969 A), mutants having resistance to isoleucine analogues such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

<2> Production Method

The microorganism which is obtained as described above is cultured in a medium in which the phosphorus concentration is at such a level to induce expression by the pho regulon promoter, to produce and accumulate an L-amino acid in the culture. Then, the L-amino acid is collected from the medium, and the L-amino acid can be efficiently produced.

In the culture of the microorganism, if a nutrient that cannot be biosynthesized by the microorganism or an element required for biosynthesis of a nutrient is depleted, growth of the microorganism is arrested. There are many substances which have this effect, and the growth of a microorganism can be restricted by the depletion of the substance. Therefore, when phosphorus is the initial growth rate-limiting factor among all the nutrients required for growth of the bacteria, the medium containing this amount of phosphorus is defined as the medium in which the phosphorus concentration is limited. Furthermore, the concentration at which the expression of the gene of interest by the pho regulon promoter is induced is called the "limited phosphorus concentration".

Although the medium may be any medium so long as it contains a carbon source and a nitrogen source, the phosphorus concentration in the medium is adjusted to the limited phosphorus concentration. Although "phosphorus" may refer any substance containing phosphorus, phosphoric acid is especially preferred, and it is preferably added in the form of a phosphoric acid salt. Such a phosphoric acid salt is not particularly limited, and it may be ammonium salt, calcium salt, or sodium salt. Potassium dihydrogenphosphate, dipotassium hydrogenphosphate, phosphoric acid polymers such as pyrophosphoric acid and so forth are used. The medium may contain one or two or more of these substances. The limited phosphorus concentration may be any concentration so long as the pho regulon promoter is activated to a higher degree as compared with a medium containing a large amount of phosphorus (namely, containing phosphorus at such a concentration that phosphorus does not act as the growth rate-limiting factor). Specifically, the concentration of phosphorus contained in the fermentation medium is usually controlled to be preferably 200 µM or lower, more preferably 150 µM or lower, further preferably 100 µM or lower, still more preferably 10 µM or lower, particularly preferably 4 µM or lower.

During the second half of the culture, the phosphorus concentration in the medium may be 0.

It is sufficient that the fermentation medium contains the least amount of phosphorus which is absolutely necessary for growth of the microorganism, and a transient phosphorus deficient state may occur. The term "transient" means that the medium may be in this phosphorus deficient state, for example, for about 20%, 40%, or 60% at most, of the total fermentation period. During the phosphorus deficient state, it is preferred that the concentration of phosphorus in the medium is 0.001 µM or higher, preferably 0.005 µM or higher, more preferably 0.01 µM or higher, still more preferably 0.05 µM or higher.

A batch culture, fed-batch culture, and continuous culture may be used. Furthermore, in order to maintain the production of the L-amino acid at a certain level or higher, the culture may be performed step-by-step as seed culture and a main culture. The seed culture may be performed with shaking in a flask or the like, or batch culture, and the main culture may be performed by a fed-batch culture or a continuous culture. Alternatively, both the seed culture and the main culture may be performed by batch culture.

The "initial medium" means the medium used for the batch culture before starting the feeding of the medium, and the "feed medium" means the medium supplied to the fermentation tank during the fed-batch culture. Furthermore, the "fermentation medium" means the medium in the fermentation tank, and the L-amino acid is collected from this fermentation medium. The "fermentation tank" means the vessel in which the L-amino acid fermentation is performed, and a tank or a jar fermenter may be used. Furthermore, any volume may be present in the fermentation tank so long as the L-amino acid can be produced and collected.

Phosphorus may be adjusted so that it is at the limited phosphorus concentration in the initial medium or the feed medium, or in both. For example, when the phosphorus concentration is limited in the fed-batch culture, the phosphorus concentration in the fermentation medium is controlled to be 200 µM or lower, preferably 150 µM or lower, more preferably 100 µM or lower, still more preferably 10 µM or lower, particularly preferably 4 µM or lower.

Furthermore, both the initial medium and the feed medium may contain phosphorus, and the phosphorus concentration of the feed medium may be different from that of the starting medium.

The phosphorus concentration is preferably controlled to be the limited phosphorus concentration in the second half of the culture, which is the L-amino acid production phase. For example, when there are two stages to the fermentation, for example, the proliferation stage and the production stage, the phosphorus concentration may be controlled so that it is the limited phosphorus concentration in the L-amino acid production phase, however it may exceed the limited phosphorous concentration or the limited phosphorous concentration may be maintained during the proliferation phase, when the L-amino acid is accumulating in the medium. Furthermore, even during the production stage, the phosphorus content does not need to be in the aforementioned range for the entire production stage, and it may be controlled to exceed the aforementioned range early in the production stage, and may decrease with time.

The second half of the culture mainly means the amino acid production phase, and it is distinguished from the cell proliferation phase. The "proliferation phase" means the period where phosphorus is mainly used for cell growth, for example, the period where the microorganism logarithmically proliferates, over 3 hours, preferably 6 hours, particularly preferably 10 hours, from the start of the culture. The "second half of culture" means the period where the carbon source is mainly used for the L-amino acid production over 6 hours, preferably 10 hours, particularly preferably 20 hours, until the end of the culture.

The carbon source in the medium may include saccharides such as glucose, glycerol, fructose, sucrose, maltose, mannose, galactose, starch hydrolysate and molasses. Glucose and sucrose are particularly preferred. In addition, organic acids such as acetic acid and citric acid and alcohols such as ethanol can also be used independently or in combination with another carbon source. Furthermore, raw materials of the carbon source may be used, and include cane molasses, beet molasses, high test molasses and citrus molasses, and hydrolysates of natural raw materials such as cellulose, starch, corn, cereal, and tapioca. Furthermore, carbon dioxide dissolved in the culture medium can also be used. These carbon sources can be used in the starting medium and the feed medium. Furthermore, the same carbon source may be used for the starting medium and the feed medium, or the carbon source of the feed medium may be different from that of the starting medium. For example, glucose may be used as a carbon source of the starting medium, while sucrose may be used as the carbon source of the feed medium.

The nitrogen source in the medium may include ammonia, ammonium salts such as ammonium sulfate, ammonium carbonate, ammonium chloride, ammonium phosphate, ammonium acetate and urea, nitrates, and so forth. Ammonia gas and aqueous ammonia used to adjust the pH can also be utilized as the nitrogen source. Furthermore, peptone, yeast extract, meat extract, malt extract, corn steep liquor, soybean hydrolysate, and so forth can also be utilized. These nitrogen sources can be used for both the starting medium and the feed medium. Furthermore, the same nitrogen source can be used for both the initial medium and the feed medium, and the nitrogen source of the feed medium may be different from that of the starting medium.

The medium preferably contains a sulfur source in addition to the carbon source, nitrogen source, and phosphorus source. Although the sulfur source may be any substance so long as it contains sulfur, sulfates such as thiosulfates and sulfites and sulfur containing amino acids such as cysteine, cystine and glutathione are desirable, and ammonium sulfate is especially desirable.

The medium may contain a growth promoting factor in addition to the carbon source, nitrogen source, and phosphorus source. Growth promoting factors such as trace metals, amino acids, vitamins, fatty acids, nucleic acids as well as peptone, casamino acid, yeast extract, soybean protein degradation product, and so forth, and substances containing these factors can be used.

Examples of the trace metals include iron, manganese, magnesium, calcium and so forth. Examples of the vitamins include vitamin $B_1$, vitamin $B_2$, vitamin $B_6$, nicotinic acid, nicotinic acid amide, vitamin $B_{12}$ and so forth. These growth inducing factors may be contained in either the initial medium or the feed medium.

When an auxotrophic mutant that requires an amino acid or the like for growth is used, it is preferable to supplement with the required nutrients in the medium.

The culture is usually performed with aeration at a fermentation temperature of 20 to 45° C., particularly preferably at 33 to 42° C. The oxygen concentration is usually adjusted to 5 to 50%, preferably about 10%. Furthermore, the aeration culture is usually performed with the pH adjusted to 5 to 9. If the pH is lowered during the culture, for example, calcium carbonate or an alkali such as ammonia gas and aqueous ammonia is added to neutralize the culture. When the culture is performed under such conditions preferably for about 10 to 120 hours, a marked amount of L-amino acid accumulates in the culture medium. Although the concentration of produced L-amino acid is not limited so long as it is higher than that observed with wild-type or parent strains, and the L-amino acid can be isolated and collected from the medium, it should be 50 g/L or higher, preferably 75 g/L or higher, more preferably 100 g/L or higher.

The L-amino acid can be collected by a known method from the medium after the culture. For example, after bacterial cells are removed from the culture medium by centrifugation or the like, the L-amino acid can be collected by concentration or crystallization.

EXAMPLES

Hereafter, the present invention will be more specifically explained with reference to the following non-limiting examples.

Example 1

(1) Culture of the L-lysine-Producing *Escherichia coli* Strain Under Phosphorus Restricted Conditions The lysine producing ability of the *Escherichia coli* strain WC196 (FERM BP-5252) was evaluated. The strain was cultured in a medium containing 40 g/L of glucose, 1 g/L of $MgSO_4$ heptahydrate, 0, 0.125, 0.5 or 1 g/L of $KH_2PO_4$, 16 g/L of $(NH_4)_2SO_4$, 10 mg/L of $FeSO_4$ heptahydrate, 10 mg/L of $MnSO_4$ tetra- or pentahydrate, 2 g/L of yeast extract and 50 g/L of $CaCO_3$ in a 500 mL-volume Sakaguchi flask. The volume of the medium at the start of the culture was 20 mL, and the culture was performed at 37° C. with reciprocal shaking at a revolving speed of 120 rpm.

Everything used in the culture, including the medium, was sterilized by autoclaving prior to the start. During the culture, cell density, glucose concentration, and the amount of L-lysine which accumulated in the medium were measured. The cell density (OD600) was obtained by measuring turbidity at 600 nm with a spectrophotometer (Beckman) when the medium was diluted with 0.1 N hydrochloric acid at appropriate intervals. The residual glucose concentration and L-lysine concentration were measured with a Biotech Analyzer (Sakura Seiki) in the supernatant of the medium obtained by removing the cells by centrifugation and diluting with water at appropriate intervals. The culture was performed for 24 to 65 hours until all the glucose in the medium was consumed.

As shown in Table 2 mentioned below, when the culture was performed with 0.5 or 1.0 g/L of $KH_2PO_4$, eventually substantially the same cell amounts were observed, as indicated with OD600. However, when the culture was performed with 0 or 0.125 g/L of $KH_2PO_4$, eventually, the cell amounts decreased. This was thought to be due to an insufficient amount of, for example, phosphorus during the middle time of the culture. Furthermore, when the culture was performed with 0 or 0.125 g/L of $KH_2PO_4$, lysine accumulation also decreased compared with the control (1.0 g/L). Incidentally, the culture medium contained phosphorus derived from yeast extract in an amount of about 0.25 g/L in the form of $KH_2PO_4$, in addition to the phosphorus derived from $KH_2PO_4$.

That is, it was demonstrated that, under phosphorus-restricted conditions, the growth of the L-lysine-producing bacterium decreased, and the bacterium's ability to produce L-lysine also decreased.

(2) Gene Expression Analysis in *Escherichia coli* Wild-Type Strain

The *Escherichia coli* wild-type strain MG1655 was cultured in a medium containing 22.2 mM glucose, 50 mM NaCl, 0.523 mM $NH_4Cl$, 1 mM $(NH_4)_2SO_4$, 0.01 mM $FeSO_4.7H_2O$, 0.005 mM $CaCl_2$, 0.01 mM $MnSO_4.4$ or $5H_2O$, 1 mM thiamine-HCl, 40 mM MOPS-KOH (pH 7.2), and a varying concentration of $KH_2PO_4$ in a 500 mL-volume Sakaguchi flask. The culture was performed with a $KH_2PO_4$ concentration of 1 mM (a phosphate-sufficient condition), or 50 μM (a phosphate-insufficient condition). The volume of the medium at the start of the culture was 20 mL, and the culture was performed at 37° C. with reciprocal shaking at a revolving speed of 120 rpm. Everything, including the medium, was sterilized by autoclaving prior to the start.

The culture medium was sampled in a volume of about 10 mL from the flask during the logarithmic phase under the phosphate-sufficient conditions, and 2 hours after the completion of proliferation due to the depletion of phosphate, and so under phosphate-insufficient conditions. Each sample was immediately cooled on ice and centrifuged in a refrigerated centrifugation machine at 10000×g for 2 minutes, and the culture supernatant was removed. Total RNA was collected from the cells by using the RNeasy Kit of QIAGEN according to the manufacturer's protocol. It was confirmed by agarose gel electrophoresis that the RNA was not degraded, and the concentration was quantified by measuring absorbance in the ultraviolet region. The RNA was stored at −80° C., and used for the subsequent gene expression analysis using a DNA macroarray.

A reverse transcription reaction was performed by using the Reverse Transcription Kit produced by Promega with 20 μg of the RNA as the template, as well as 1 mM each of dATP, dGTP and dTTP, and dCTP labeled with $^{33}P$ in an amount of 1500 MBq in terms of specific radioactivity as substrates to obtain labeled cDNA of each phase.

The cDNA was hybridized with an *Escherichia coli* macroarray membrane produced by Genosys according to the protocol for the membrane, and the membrane was washed after the completion of the hybridization. The washed membrane was sealed, brought into contact with an imaging plate for 48 hours in the dark, and exposed. The exposed imaging plate was visualized with a fluoroimaging analyzer, FLA-3000G, produced by Fuji Photo Film, and the obtained visualized image was transferred to a DNA array image analysis system AIS to quantify the concentration of each spot and obtain gene expression profile data for each phase.

Using the profile data, genes were searched for which are from the saccharide metabolism and lysine biosynthesis systems, and in particular genes showing a high expression level in the logarithmic phase, but showing a reduced expression level when the proliferation phase was completed due to the depletion of phosphorus by the Student's t-test were sought. As a result, it was found that gene expression of the lysA gene was significantly decreased (Table 3). Furthermore, genes showing low expression level in the logarithmic phase, but showing an increased expression level when the proliferation was completed due to depletion of phosphorus by the Student's t-test were looked for in the entire genome of *Escherichia coli*. As a result, it was found that gene expression of the phoA gene was significantly increased (Table 3).

The phosphate concentration in the medium was analyzed in the medium subjected to centrifugation at 10000 rpm for 2 minutes and diluted to an appropriate concentration, by using the P Test Wako (Wako Pure Chemical Industries).

(3) Construction of Strain in which the lysA Gene Ligated to the phoA Gene Promoter is Amplified The lysA gene ligated to the promoter of the phoA gene (henceforth abbreviated as PphoA-lysA) was constructed by crossover PCR (described in Link A. J., Phillips D., Church G. M., J. Bacteriol., Vol. 179, pp. 6228-6237, 1997). PCR was performed with the primers LysA-1 and LysA-2 (SEQ ID NOS: 22 and 23), and phoAp-1 and phoAp-2 (SEQ ID NOS: 26 and 27) shown in Table 4, respectively, and genomic DNA from the *E. coli* K-12 strain as the template. Both the primers LysA-1 and LysA-2, and phoAp-1 and phoAp-2 were used in a molar ratio 10:1. A second PCR was performed with the PCR product obtained in the first PCR as the template and the primers LysA-1 and phoAp-1. This PCR product was digested with BamHI and HindIII, and combined with pMW118 (Nippon Gene) which had been digested with BamHI and HindIII, and a ligation reaction was performed by using the DNA Ligation Kit ver. 2 (Takara Shuzo). The DH5α competent cells (Takara Shuzo) were transformed with the ligation reaction solution, and the cells were inoculated onto an LB agar plate (LB+Ap plate) containing 50 μg/mL of ampicillin (Ap, Nakalai Tesque), and colonies were selected at 37° C. The colonies were cultured at 37° C. in the LB medium containing 50 μg/mL of Ap in a test tube, and plasmids were extracted with Wizard Plus Miniprep (Promega). The extracted plasmids were digested with BamHI and HindIII, and the plasmid in which a sequence of the desired length was inserted was selected to construct the pMW-PphoA-lysA plasmid.

The *E. coli* WC1-96 strain was transformed with the pMW-PphoA-lysA plasmid to obtain the WC196/pMW-PphoA-lysA strain.

(4) Construction of the Strain with Amplified lysA and lysR Genes

PCR was performed with the primers LysA-3 and LysA-4 (SEQ ID NOS: 24 and 25) shown in Table 4 and genomic DNA from the *E. coli* K-12 strain as the template. The PCR product was digested with BamHI and HindIII, and combined with pMW118 (Nippon Gene) which had been digested with BamHI and HindIII, and a ligation reaction was performed with the DNA Ligation Kit ver. 2 (Takara Shuzo). DH5α competent cells (Takara Shuzo) were transformed with the ligation reaction solution, and the cells were inoculated on an LB agar plate (LB+Ap plate) containing 50 μg/mL of ampicillin (Ap, Nakalai Tesque). Colonies were selected at 37° C. The colonies were cultured at 37° C. in LB medium containing 50 μg/mL of Ap in a test tube, and plasmids were extracted with Wizard Plus Miniprep (Promega). The extracted plasmids were digested with BamHI and HindIII, and the plasmid in which the sequence of the desired length was inserted was selected to construct the pMW-lysAR plasmid.

The *E. coli* WC196 strain was transformed with the pMW-lysAR plasmid to obtain the WC196/pMW-lysAR strain.

(5) L-lysine Production by Two lysA Gene-Amplified Strains

The ability of the strains prepared in (3) and (4) above to produce L-lysine, and using WC196/pMW118 1 (only the vector) as a control was evaluated. Each strain was cultured in a medium containing 40 g/L of glucose, 1 g/L of $MgSO_4$ heptahydrate, 0, 0.125 or 1 g/L of $KH_2PO_4$, 16 g/L of $(NH_4)_2SO_4$, 10 mg/L of $FeSO_4$ heptahydrate, 10 mg/L of $MnSO_4$ tetra- or pentahydrate, 2 g/L of yeast extract, 50 g/L of $CaCO_3$ and 100 μg/mL of ampicillin in a 500 mL-volume Sakaguchi flask. As mentioned in (1) above, phosphorus was considered restricted when 0 or 0.125 g/L of $KH_2PO_4$ was present and phosphorus was considered sufficient when 1 g/L of $KH_2PO_4$ was present. The volume of the medium at the start of the culture was 20 mL, and the culture was performed at 37° C. with reciprocal shaking at a revolving speed of 120 rpm. Everything, including the medium, was sterilized by autoclaving prior to use. During the culture, cell density, glucose concentration and the amount of accumulated L-lysine in the medium were measured. The cell density (OD600) was obtained by measuring turbidity at 600 nm with a spectrophotometer (Beckman) for the medium diluted with 0.1 N hydrochloric acid at appropriate intervals. The residual glucose concentration and lysine concentration were measured at appropriate intervals with a Biotech Analyzer (Sakura Seiki) in the supernatant of the medium obtained by removing the cells by centrifugation and diluting with water. The culture was performed for 24 to 65 hours until all the glucose in the medium was consumed.

The results are shown in Table 5. When phosphorus is present in sufficient amounts throughout the culture period, and is not present in a growth-limiting amount (1 g/L of $KH_2PO_4$), all the strains were substantially equivalent in growth and lysine accumulation. In contrast, when phosphorus was depleted in the middle of the culture period, and therefore is present in a growth-limiting amount (0 or 0.125 g/L of $KH_2PO_4$), the control strain and WC196/pMW-lysAR had reduced lysine production, WC196/pMW-PphoA-lysA had markedly increased lysine production compared with the foregoing strains. That is, it was confirmed that the lysine-producing ability was improved when the amount of phosphorus was limited in the culture by introducing the lysA gene expressed by the phoA promoter.

TABLE 2

Lysine-producing ability of *Escherichia coli* strain WC196 under various $KH_2PO_4$ concentration conditions

| $KH_2PO_4$(g/L) | 1 | 0.5 | 0.125 | 0 |
|---|---|---|---|---|
| OD600 | 20.82 | 21.00 | 16.91 | 9.87 |
| Lys (g/L) | 1.21 | 1.16 | 0.63 | 0.39 |

TABLE 3

Expression of lysA gene and phoA gene under phosphorus-sufficient conditions and phosphorus-limited conditions

| | Gene expression intensity (normalized) | | | | | | |
|---|---|---|---|---|---|---|---|
| Gene | Phosphate-sufficient condition (n = 4) | | | | Phosphate-limited condition (n = 2) | | P value in t-test |
| lysA | 14.27 | 14.57 | 12.04 | 11.78 | 4.51 | 3.84 | 0.0014 |
| phoA | 24.98 | 24.26 | 26.47 | 18.17 | 624.66 | 565.3 | 6.38E−06 |

TABLE 4

List of used primers
(SEQ ID NOS: 22 to 27 from the top)

| lysA-1 | GCGGATCC TCCATGCCAAAATGATCCCGGATGCTGA |
|---|---|
| lysA-2 | GACAAAAGCCCGGACACCAGAAATGCCACATTCACTGTTCAGCACCG |
| lysA-3 | GAAAGCTT GCGCAGTGTTTTGCCTGTGT |
| lysA-4 | GCGGATCCGGTATGGTGCTGATCAACCGTATCCTGCCT |
| PphoA-1 | GCAAGCTTATGCGGTGAGTTTTTTTCTCTTAATTAT |
| PphoA-2 | CGGTGCTGAACAGTGAATGTGGCAT TTCTGGTGTCCGGGCTTTTGTC |

TABLE 5

Lys production in WC196 in which the lysA gene is ligated with the phoA promoter, andis amplified under phosphorus-restricted conditions

| | $KH_2PO_4$ (g/L) | | | | | | | | |
|---|---|---|---|---|---|---|---|---|---|
| | 1 | | | 0.125 | | | 0 | | |
| Plasmid | pMW118 | pMW-lysAR | pMW-PphoA-lysA | pMW118 | pMW-lysAR | pMW-PphoA-lysA | pMW118 | pMW-lysAR | pMW-PphoA-lysA |
| OD600 | 24.76 | 25.70 | 24.00 | 16.81 | 18.47 | 20.21 | 10.10 | 11.31 | 12.91 |
| Lys(g/L) | 1.21 | 1.29 | 1.32 | 1.14 | 1.20 | 1.65 | 0.44 | 0.52 | 0.74 |

Example 2

(1) Construction of L-phenylalanine-Producing Strain

Figure 3:
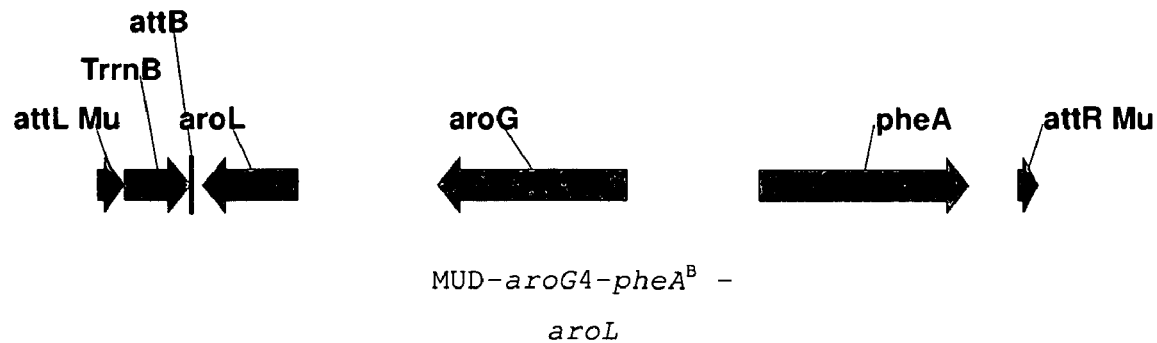
FIG. 3 shows the structure of the fragment integrated into the MG1655ΔtyrAΔtyrR,$P_L$-yddG,MUD-aroG4-pheA$^B$-aroL strain.

E. coli strain MG1655ΔtyrAΔtyrR,P$_L$-yddG was constructed in the same way as the previously-described E. coli strain BW25113 (WO03044192A1). The cassette MUD-aroG4-pheA$^B$-aroL-Cm$^R$ was integrated into the chromosome using the helper plasmid pHT10 (manufactured by Funakoshi). Then, the marker Cm$^R$ flanked by attR and attL of phage λ was excised using the helper plasmid pMW-int-his (WO05/010175). The structure of resulting fragment, which is integrated into the bacterial chromosome, is shown in FIG. 3. The sequence of this fragment is shown in SEQ ID NO: 30. Genes aroG4 and pheA$^B$ are mutated alleles of the E. coli genes aroG and pheA, respectively, and encode enzymes resistant to Phe inhibition (EP 0488424B, JP03225597B, JP03060668B). All genes are under the control of their native promoters. In the case of the pheA$^B$ gene, the attenuator was deleted. The point of integration of the cassette was determined. Its coordinate (corresponding to the left Mu end) is 4581838 on the E. coli physical map. Thus, strain MG1655ΔtyrAΔtyrR,P$_L$-yddG,MUD-aroG4-pheA$^B$-aroL was obtained.

The other strain, MG1655ΔtyrAΔtyrR,P$_L$-yddG,MUD-(P$_{PhoA}$-aroG4)-pheA$^B$-aroL, was constructed via λ Red mediated integration (Datsenko, K. A. and Wanner, B. L., Proc. Natl. Acad. Sci. USA, 2000, 97(12), 6640-6645) of the promoter P$_{PhoA}$ upstream of the aroG4 gene in the chromosome of the strain.

Figure 4:
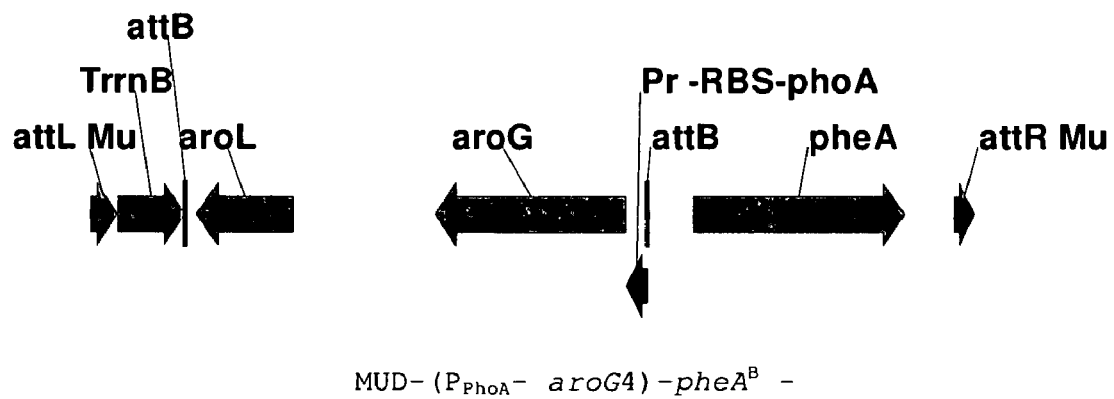
FIG. 4 shows the structure of the fragment integrated into the MG1655ΔtyrAΔtyrR,$P_L$-yddG,MUD-($P_{phoA}$-aroG4)-pheA$^B$-aroL strain.

To integrate the promoter P$_{phoA}$, a DNA fragment containing the promoter of the phoA gene was amplified on the chromosome of the MG1655 strain by PCR using the primers SEQ ID NOs: 31 and 32. The primer of SEQ ID NO: 31 contains a BglII site at the 5'-end, which is necessary to join another fragment containing the chloramphenicol marker. The primer of SEQ ID NO: 32 has 36 nucleotides which are complementary to the 5'-end region of the aroG gene which are necessary for integration into the chromosome using the λ Red system. The DNA fragment containing the Cm$^R$ marker encoded by the cat gene was obtained by PCR, using the primers of SEQ ID NOs: 33 and 34, and pMW118-attL-Cm-attR as the template (WO 05/010175). The primer of SEQ ID NO: 33 contains a BglII site at the 5'-end, which is necessary to join the above fragment containing the promoter of phoA gene. The primer of SEQ ID NO: 34 contains 36 nucleotides complementary to the 5'-end region of the aroG gene, which is necessary for integration into the chromosome using the λ Red system. The two PCR fragments were treated with the BglII restrictase and ligated together. The ligated product was amplified by PCR using primers of SEQ ID NO: 32 and 34 and integrated into the chromosome of the MG1655ΔtyrAΔtyrR,P$_L$-yddG,MUD-aroG4-pheA$^B$-aroL strain. Then, the marker Cm$^R$ flanked by attR and attL of phage λ was excised using the helper plasmid pMW-int-his (WO05/010175). Thus, strain MG1655ΔtyrAΔtyrR,P$_L$-yddG,MUD-(P$_{phoA}$-aroG4)-pheA$^B$-aroL was obtained. The structure of the resulting fragment which was integrated into the bacterial chromosome is shown in FIG. 4. The sequence of this fragment is shown in SEQ ID NO: 35.

(2) Production of L-phenylalanine

Both of these above-described strains differ only in the regulation of aroG4 gene: constitutive in Cassette MUD-aroG4-pheA$^B$-aroL and regulated by phosphate availability in MUD-(P$_{PhoA}$-aroG4)-pheA$^B$-aroL. The aroG4 gene product catalyses the first reaction of the aromatic pathway, so its activity is crucial for redirection of the carbon flow to the biosynthesis of aromatic compounds (Phe, for example). Testing of both of the above-described L-phenylalanine-producing strains was performed in a tube fermentation using a medium of the following composition (Table 6).

TABLE 6

| Medium composition for test tube fermentation. | |
|---|---|
| Component | Concentration, g/l |
| Glucose | 40 |
| MgSO$_4$ | 1 |
| CaCO$_3$ | 30 |
| Yeast extract | 2 |
| (NH$_4$)$_2$SO$_4$ | 16 |
| L-Tyr | 0.125 |
| KH$_2$PO$_4$ | 1/0.6/0.4 |
| FeSO$_4$ | 0.01 |
| MnSO$_4$ | 0.01 |

The concentration of KH$_2$PO$_4$ was varied. Fermentation was stopped when glucose was consumed (~30 h). The results of the fermentation (six independent experiments) is shown in Table 7.

TABLE 7

| Test tube fermentation. | | | |
|---|---|---|---|
| Strain | KH$_2$PO$_4$, g/l | OD 540 nm | Phe, g/l |
| MG1655ΔtyrAΔtyrR, P$_L$-yddG, MUD-aroG4-pheA$^B$-aroL (I) | 1 | 24 ± 1 | 3.9 ± 0.2 |
| | 0.6 | 23 ± 1 | 5.0 ± 0.2 |
| | 0.4 | 22 ± 1 | 5.5 ± 0.1 |
| MG1655ΔtyrAΔtyrR, P$_L$-yddG, MUD-(P$_{PhoA}$-aroG4)-pheA$^B$-aroL (II) | 1 | 25 ± 1 | 3.3 ± 0.2 |
| | 0.6 | 23 ± 1 | 7.2 ± 0.2 |
| | 0.4 | 22 ± 1 | 7.5 ± 0.3 |

As seen from Table 7, for strain (II), L-phenylalanine biosynthesis was reduced when phosphate was present in the medium at a high concentration, and increased when the amount of phosphate was limited. Indeed, under excess phosphate conditions (1 g/l of KH$_2$PO$_4$), the final cell density of strain I was slightly lower than the density of strain II. This fact correlates with the lower L-phenylalanine production for strain II in comparison with strain I. When phosphate is limited (0.6 and 0.4 g/l), the final cell density was lower, and was equal for both strains. Both strains produced more L-phenylalanine under phosphate limiting conditions in comparison with their production under excess phosphate conditions, but strain II produced significantly more L-phenylalanine than strain I. Higher L-phenylalanine production in both strains is explained by the prolonged stationary phase which is induced by the limited phosphate. The significant higher capacity of L-phenylalanine biosynthesis of strain II is explained by higher activity of DAHP synthase, especially in stationary phase.

INDUSTRIAL APPLICABILITY

According to the present invention, an improved method for producing an L-amino acid such as L-lysine and L-phenylalanine is provided.

Explanation of sequences:
SEQ ID NO: 1: phoA gene promoter sequence (500 bp of region upstream of start codon)
SEQ ID NO: 2: phoA gene promoter sequence (GenBank)
SEQ ID NO: 3: phoB gene promoter sequence (500 bp of region upstream of start codon)
SEQ ID NO: 4: phoB gene promoter sequence (GenBank)
SEQ ID NO: 5: phoE gene promoter sequence (500 bp of region upstream of start codon)
SEQ ID NO: 6: phoE gene promoter sequence (GenBank)
SEQ ID NO: 7: phoH gene promoter sequence (500 bp of region upstream of start codon)
SEQ ID NO: 8: phoH gene promoter sequence (GenBank)
SEQ ID NO: 9: asr gene promoter sequence (500 bp of region upstream of start codon)
SEQ ID NO: 10: asr gene promoter sequence (GenBank)
SEQ ID NO: 11: argP gene promoter sequence (500 bp of region upstream of start codon)
SEQ ID NO: 12: argP gene promoter sequence (GenBank)
SEQ ID NO: 13: ugpB gene promoter sequence (500 bp of region upstream of start codon)
SEQ ID NO: 14: ugpB gene promoter sequence (GenBank)
SEQ ID NO: 15: pstS gene promoter sequence (500 bp of region upstream of start codon)
SEQ ID NO: 16: pstS gene promoter sequence (GenBank)
SEQ ID NO: 17: psiE gene promoter sequence (500 bp of region upstream of start codon)
SEQ ID NO: 18: psiE gene promoter sequence (GenBank)
SEQ ID NO: 19: phnC gene promoter sequence (500 bp of region upstream of start codon)
SEQ ID NO: 20: phnC gene promoter sequence (GenBank)
SEQ ID NO: 21: pho box
SEQ ID NO: 22: Primer for lysA gene amplification
SEQ ID NO: 23: Primer for lysA gene amplification
SEQ ID NO: 24: Primer for lysA gene amplification
SEQ ID NO: 25: Primer for lysA gene amplification
SEQ ID NO: 26: Primer for phoA gene promoter amplification
SEQ ID NO: 27: Primer for phoA gene promoter amplification
SEQ ID NO: 28: lysA gene
SEQ ID NO: 29: Amino acid sequence encoded by lysA gene
SEQ ID NO: 30: Fragment integrated into MG1655ΔtyrAΔtyrR,$P_L$-yddG,MUD-aroG4-pheA$^B$-aroL strain
SEQ ID NO: 31: Primer for amplification of DNA fragment containing phoA gene promoter
SEQ ID NO: 32: Primer for amplification of DNA fragment containing phoA gene promoter
SEQ ID NO: 33: Primer for amplification of DNA fragment containing Cm$^R$ marker
SEQ ID NO: 34: Primer for amplification of DNA fragment containing Cm$^R$ marker
SEQ ID NO: 35: Fragment integrated into MG1655ΔtyrAΔtyrR,$P_L$-yddG,MUD-($P_{phoA}$-aroG4)-pheA$^B$-aroL strain
SEQ ID NO: 36: aroG gene
SEQ ID NO: 37: Amino acid sequence encoded by aroG gene (3-deoxy-D-arabinoheptulonate-7-phosphate synthase)
SEQ ID NO: 38: aroL gene
SEQ ID NO: 39: Amino acid sequence encoded by aroL gene (shikimate kinase)
SEQ ID NO: 40: pheA gene
SEQ ID NO: 41: Amino acid sequence encoded by pheA gene (prephenate dehydratase, chorismate mutase)

We claim:

1. A method for producing an L-amino acid comprising:
   A) culturing in a medium a microorganism belonging to the Enterobacteriaceae family and having the ability to produce an L-amino acid, and
   B) collecting the L-amino acid from the medium,
   wherein a DNA fragment comprising:
   i) a pho regulon promoter, and
   ii) a structural gene encoding an L-amino acid biosynthetic enzyme is introduced into said microorganism,
   wherein said gene is ligated downstream of the promoter so that the gene is expressed by the promoter, and
   wherein the activity of the L-amino acid biosynthetic enzyme is increased when the gene is expressed by the promoter, and wherein the phosphorus concentration in the medium is limited such that the production of the amino acid is increased under the limited phosphorous conditions compared with that under excess phosphorous conditions.

2. The production method according to claim 1, wherein the pho regulon promoter is the promoter of a gene selected from the group consisting of phoA, phoB, phoE, phoH, asr, argP, ugpB, pstS, psiE, and phnC.

3. The production method according to claim 1, wherein the pho regulon promoter comprises a pho box.

4. The production method according to claim 1, wherein the phosphorus concentration in the medium is 200 µM/L or lower.

5. The production method according to claim 1, wherein the expression level of the L-amino acid biosynthetic enzyme decreases when phosphorus is depleted in the medium.

6. The method according to claim 1, wherein the DNA fragment is present on a multi-copy vector in the microorganism, or is introduced into the chromosomal DNA of the microorganism.

7. The method according to claim 1, wherein the microorganism belonging to the Enterobacteriaceae family is selected from the group consisting of *Escherichia bacteria*, *Enterobacter bacteria*, *Pantoea bacteria*, *Klebsiella* bacteria, and *Serratia* bacteria.

8. The method according to claim 1, wherein the L-amino acid is selected from the group consisting of L-lysine, L-threonine, L-tryptophan, L-phenylalanine, L-glutamic acid, and combinations thereof.

9. The method according to claim 8, wherein the L-amino acid is L-lysine, and the L-amino acid biosynthetic enzyme is selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyl diaminopimelate deacylase, and combinations thereof.

10. The method according to claim 8, wherein the L-amino acid is L-threonine, and the L-amino acid biosynthetic enzyme is selected from the group consisting of aspartokinase III, aspartate semialdehyde dehydrogenase, aspartokinase I, homoserine kinase, threonine synthase encoded by the thr operon, and combinations thereof.

11. The method according to claim 8, wherein the L-amino acid is L-glutamic acid, and the L-amino acid biosynthetic enzyme is selected from the group consisting of glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, 6-phosphogluconate dehydratase, 2-keto-3-deoxy-6-phosphogluconate aldolase, and combinations thereof.

12. The method according to claim 8, wherein the L-amino acid is L-tryptophan or L-phenylalanine, and the L-amino acid biosynthetic enzyme is selected from the group consisting of 3-deoxy-D-arabinoheptulonate-7-phosphate synthase, 3-dehydroquinate synthase, shikimate dehydratase, shikimate kinase, 5-enolpyruvylshikimate 3-phosphate synthase, chorismate synthase, prephenate dehydratase, chorismate mutase, and combinations thereof.

* * * * *

```
                       SEQUENCE LISTING

<160> NUMBER OF SEQ ID NOS: 41

<210> SEQ ID NO 1
<211> LENGTH: 81
<212> TYPE: DNA
<213> ORGANISM: Escherichia coli

<400> SEQUENCE: 1
aaagttaatc ttttcaacag ctgtcataaa gttgtcacgg ccgagactta tagtcgcttt    60 gttttattt tttaatgtat t                                               81

<210> SEQ ID NO 2
<211> LENGTH: 500
<212> TYPE: DNA
<213> ORGANISM: Escherichia coli

<400> SEQUENCE: 2
gagaaacgtt tcgctggtaa tcaaacaaaa aatatttgcg caaagtatt cctttgtcat     60 aaaaataata cttccagaca ctatgaagtt gtgaaacata atgttaactt ctccatactt   120
tggataagga aatacagaca tgaaaatct cattgctgag ttgttattta agcttgccca    180
aaaagaagaa gagtcgaaag aactgtgtgc gcaggtagaa gctttggaga ttatcgtcac   240
tgcaatgctt cgcaatatgg cgcaaaatga ccaacagcgg ttgattgatc aggtagaggg   300
ggcgctgtac gaggtaaagc ccgatgccag cattcctgac gacgatacgg agctgctgcg   360
cgattacgta aagaagttat tgaagcatcc tcgtcagtaa aaagttaatc ttttcaacag   420
```

```
ctgtcataaa gttgtcacgg ccgagactta tagtcgcttt gtttttattt tttaatgtat      480
ttgtacatgg agaaaataaa                                                  500

<210> SEQ ID NO 3
<211> LENGTH: 81
<212> TYPE: DNA
<213> ORGANISM: Escherichia coli

<400> SEQUENCE: 3
tgaagatatg tgcgacgagc ttttcataaa tctgtcataa atctgacgca taatgacgtc      60
gcattaatga tcgcaaccta t                                                81

<210> SEQ ID NO 4
<211> LENGTH: 500
<212> TYPE: DNA
<213> ORGANISM: Escherichia coli

<400> SEQUENCE: 4
cgaccacggt agtattgagg aacgccatga tatcgcgcga ttcattcagc gtggcgaccg      60
agtcatggtt tcctgccagt accaccagat gacagccagt tgctgtaaa ttgacaacaa     120 aacggttgta taacgtgcgg gcgtaactgg gcggcgagcc ggtatcgaaa acatcaccgg     180
caacaataat cgcatccacc tgatgggttt gtgctgtctc cagcagccag tcaagaaaag     240
cctgatgttc agcttcgcgg cttttactgt agaagttctg gccgagatgc cagtctgagg     300
tgtgaaggat gcgcataacg gttccctggc gaaaaagcat gggcgcgatt atacccaaac     360
agatgtgcca tttgctttt tctgcgccac ggaaatcaat aacctgaaga tatgtgcgac     420
gagcttttca taaatctgtc ataaatctga cgcataatga cgtcgcatta atgatcgcaa     480
cctatttatt acaacagggc                                                500

<210> SEQ ID NO 5
<211> LENGTH: 81
<212> TYPE: DNA
<213> ORGANISM: Escherichia coli

<400> SEQUENCE: 5
ttttaagaat attattaatc tgtaatatat ctttaacaat ctcaggttaa aactttcct      60 gttttcaacg ggactctccc g                                                81

<210> SEQ ID NO 6
<211> LENGTH: 500
<212> TYPE: DNA
<213> ORGANISM: Escherichia coli

<400> SEQUENCE: 6
gatggtcgct ggcagttccg ggtaacccag gtgctcacgt ccggcggcga tcgcgcccga      60
cgtcacaata acaatccgat gcccggcggc atgtaactgc gcgcactggc gaacaagttc     120
aacgatatgg gcacggttca gacggcgcga tccgcctgtt agcacactgg tgccgagttt     180
taccaccagc gtctggctgt cactcatgat tctctgccat tcaattttag gaaaaatgat     240
atcaaacgaa cgttttagca ggactgtcgt cggttgccaa ccatctgcga gcaaagcatg     300
gcgttttgtt gcgcgggatc agcaagccta gcggcagttg tttacgcttt tattacagat     360
ttaataaatt accacatttt aagaatatta ttaatctgta atatatcttt aacaatctca     420
ggttaaaaac tttcctgttt tcaacgggac tctcccgctg aatattgcgc gttaattaa     480 aatcaggaat gaaaatgaaa                                                500
```

<210> SEQ ID NO 7
<211> LENGTH: 81
<212> TYPE: DNA
<213> ORGANISM: Escherichia coli

<400> SEQUENCE: 7

```
gcacacagct ttttcatca ctgtcatcac tctgtcatct ttccagtaga aactaatgtc    60
actgaaatgg tgttttatag t                                             81
```

<210> SEQ ID NO 8
<211> LENGTH: 500
<212> TYPE: DNA
<213> ORGANISM: Escherichia coli

<400> SEQUENCE: 8

```
accaacacga tctggaaaaa ggcttcctga cagtacaaaa aaggctcaat ggcgaagcgc    60
tggaggaata cgttaaacct atcggcggcg gttattttt tgcgctgccg ggggtgaagg   120
acgcgaacga ttatttcgga agcgcgttat tgcgggttta atgttttag gcggataagg   180 catttgtgcg cagatgcctg atgcgacgct tgcgcgtctt atcatgccta caatcagtgc   240
gggtttggta ggctggataa ggcgttcacg ccgcatccgg cgatcgtgca ctgatgcctg   300
atgcaaatcc tgctgaaagc acacagcttt tttcatcact gtcatcactc tgtcatcttt   360
ccagtagaaa ctaatgtcac tgaaatggtg ttttatagtt aaatataagt aaatatattg   420
ttgcaataaa tgcgagatct gttgtactta ttaagtagca gcggaagttc ccggcagtga   480
tagtcagtca ctatggagat                                              500
```

<210> SEQ ID NO 9
<211> LENGTH: 77
<212> TYPE: DNA
<213> ORGANISM: Escherichia coli

<400> SEQUENCE: 9

```
gttacacgct gaaaccaacc actcacggaa gtctgccatt cccagggata tagttatttc    60
aacggccccg cagtggg                                                  77
```

<210> SEQ ID NO 10
<211> LENGTH: 500
<212> TYPE: DNA
<213> ORGANISM: Escherichia coli

<400> SEQUENCE: 10

```
tgttttctgg cataactatg gctggaacgg cgtcggcgca tttattgctc tgatgctggt    60
cattgctctg ctggtcggga cgcgtttgca tcgtcgtctg cacgcctgaa aaataagtcc   120
ggactgcggt aaataccccgt ccggacttat tgccagctca aaccaacgtt aatagccatc   180
ctaaaataga cgaagcgcca gccaattccc gcagcgcgtc tagcgtcatc aggattataa   240
gtacccaaat aaacggattc attttgctgt gtgtcattta ttactgatgc gcagttattc   300
tactgctttg taagtagtaa aatagttaac ccgatcaaga ctactattat tggtagctaa   360
atttccctta agtcacaata cgttattatc aacgctgtaa tttattcagc gtttgtacat   420
atcgttacac gctgaaacca accactcacg gaagtctgcc attcccaggg atatagttat   480
ttcaacggcc ccgcagtggg                                              500
```

<210> SEQ ID NO 11
<211> LENGTH: 78
<212> TYPE: DNA

<213> ORGANISM: Escherichia coli

<400> SEQUENCE: 11

| gccgacggct tcggtatatg caacctgaca caaaattgtg tcatagtgca ggaaaaagca | 60 |
| tttaccagga gcagacaa | 78 |

<210> SEQ ID NO 12
<211> LENGTH: 500
<212> TYPE: DNA
<213> ORGANISM: Escherichia coli

<400> SEQUENCE: 12

| tacaccaaca atggtgccgg gctgaacata ctgaagtgcc gcccatccta ctgcttttt | 60 |
| caattcatcc tgcgtcatga tcgtttcgcc tgtggtatga aatttcacac gcattatata | 120 |
| caaaaaagc gattcagacc ccgttggcaa gccgcgtggt taactcatcc ataaaatatc | 180 |
| gcgcaatggc aggcatcccc tttcgccccg caaataaagc atacaacggt ctgggtatgc | 240 |
| cgctccacgg tgcaaacagg cgcaccagtt caccgttcgc aagcccctgt ttacaggcaa | 300 |
| attgaggcaa taacgccacg ccattcaaca caaccagggc gcgaactcgc tgagcgaaat | 360 |
| gcattagcgc aaatccctga tcttttaagc tgcgcttta accacggata caaatgttac | 420 |
| ccgccgacgg cttcggtata tgcaacctga cacaaaattg tgtcatagtg caggaaaaag | 480 |
| catttaccag gagcagacaa | 500 |

<210> SEQ ID NO 13
<211> LENGTH: 81
<212> TYPE: DNA
<213> ORGANISM: Escherichia coli

<400> SEQUENCE: 13

| tatcttacaa atgtaacaaa aaagttattt ttctgtaatt cgagcatgtc atgttacccc | 60 |
| gcgagcataa aacgcgtgaa t | 81 |

<210> SEQ ID NO 14
<211> LENGTH: 500
<212> TYPE: DNA
<213> ORGANISM: Escherichia coli

<400> SEQUENCE: 14

| ggctacgtgc tggaaaacgg ccatgtagtg cttccgata ctggtgatgc gctgctggcg | 60 |
| aatgaagcgg tgagaagtgc gtatttaggc gggtaataac acgttgattg atagggagtc | 120 |
| aaaagactcc tttgagacag gtgacaaatg taaaattgcc tgatgcgctg cgcttatcag | 180 |
| gcctactggg tgagtggcaa tatgttgaat ttgcacgatc ttgtaggcct gataaggcgt | 240 |
| ttacgccgca tccggcatga acgatgagc aatctgtaga gtttgattca gaccttctat | 300 |
| attttcccgc ttatccgtgc cccatctccc atttttccctc acccacgccg tcaccgcctt | 360 |
| gtcatctttc tgacacctta ctatcttaca aatgtaacaa aaaagttatt tttctgtaat | 420 |
| tcgagcatgt catgttaccc cgcgagcata aacgcgtga attcgcgcat tcggtacaac | 480 |
| aagagagata aacgatgaaa | 500 |

<210> SEQ ID NO 15
<211> LENGTH: 81
<212> TYPE: DNA
<213> ORGANISM: Escherichia coli

<400> SEQUENCE: 15

```
tcataaaact gtcatattcc ttacatataa ctgtcacctg tttgtcctat tttgcttctc    60
gtagccaaca aacaatgctt t                                              81

<210> SEQ ID NO 16
<211> LENGTH: 500
<212> TYPE: DNA
<213> ORGANISM: Escherichia coli

<400> SEQUENCE: 16
ggatgcgggt tttgtaagta gcgataacat gcacatcatc gagatgccgc atgtggaaga    60
ggtgattgca ccgatcttct acaccgttcc gctgcagctg ctggcttacc atgtcgcgct   120
gatcaaaggc accgacgttg accagccgcg taacctggca aaatcggtta cggttgagta   180
ataaatggat gccctgcgta agcggggcat ttttcttcct gttatgtttt taatcaaaca   240
tcctgccaac tccatgtgac aaaccgtcat cttcggctac ttttttctctg tcacagaatg   300 aaaatttttc tgtcatctct tcgttattaa tgtttgtaat tgactgaata tcaacgctta   360
tttaaatcag actgaagact ttatctctct gtcataaaac tgtcatattc cttacatata   420
actgtcacct gtttgtccta ttttgcttct cgtagccaac aaacaatgct ttatgaatcc   480
tcccaggaga cattatgaaa                                               500

<210> SEQ ID NO 17
<211> LENGTH: 80
<212> TYPE: DNA
<213> ORGANISM: Escherichia coli

<400> SEQUENCE: 17
tgaacaaaac atacacaaaa aatatagatc tccgtcacat ttttgcgtta tacaggaagc    60
tcgccactgt gaaggaggta                                                80

<210> SEQ ID NO 18
<211> LENGTH: 500
<212> TYPE: DNA
<213> ORGANISM: Escherichia coli

<400> SEQUENCE: 18
ttgcgatctg gtgtgtaaag gcgaaaacat tctgtcttcc tgtccgtcga tatcggttgc    60
aggtctggtt gcctgagcga ctgggccatc attgggctgg agacattgct ttgcggtagg   120
tcggctttat cagcagtacc gagcggacca gcataagcag gaagaacaga gactgataac   180
atcaaagcag caaataagg cttcattttt accaccttta tcaggttacg tttcatttgt    240
tccagaggaa cattgtcgat ttttcgcgca ttgctggtgg ctgggaatca cctgaatggg   300 tgattttga attaccggct ttggtgcggt ttgtcttgcc ggatgcgccg ccaggcgcgg    360
cttatccggc ctacgggtag gtatatccgg cttttggtgga ggcgcgctcc aaatccaggt  420
tgaacaaaac atacacaaaa aatatagatc tccgtcacat ttttgcgtta tacaggaagc   480
tcgccactgt gaaggaggta                                               500

<210> SEQ ID NO 19
<211> LENGTH: 81
<212> TYPE: DNA
<213> ORGANISM: Escherichia coli

<400> SEQUENCE: 19
atcgaattcc cgttaactct tcatctgtta gtcactttta attaaccaaa tcgtcacaat    60
aatccgccac gatggagcca c                                              81
```

<210> SEQ ID NO 20
<211> LENGTH: 500
<212> TYPE: DNA
<213> ORGANISM: Escherichia coli

<400> SEQUENCE: 20
tgctctataa aatcagcttc ggcgaaatgc caaaatcagc gcaggacagc gccgagaact    60
gcccttccgg aatgcaattt cccgataccg ccatcgccca cgccaatgtg cgcattgccg   120
gaagcgacat catgatgagc gatgccatgc cgtcaggaaa agccagctac tccggctta    180 cgctggtgct cgattcgcaa caggtcgaag aaggaaaacg ctggtttgac aatcttgccg   240
ctaacggaaa aatcgaaatg gcctggcagg aaactttctg ggcgcatggc tttggcaaag   300
tcaccgataa atttggcgta ccgtggatga ttaatgtcgt caaacaacaa ccaacgcaat   360
aacccgccgg gaggcccgcc ctcccgcact gtcatcgaat cccgttaac tcttcatctg   420 ttagtcactt ttaattaacc aaatcgtcac aataatccgc cacgatggag ccactttttt   480
agggaggctg catcatgcaa                                                500

<210> SEQ ID NO 21
<211> LENGTH: 18
<212> TYPE: DNA
<213> ORGANISM: Artificial Sequence
<220> FEATURE:
<223> OTHER INFORMATION: pho Box

<400> SEQUENCE: 21
ctgtcatawa wctgtmay                                                   18

<210> SEQ ID NO 22
<211> LENGTH: 36
<212> TYPE: DNA
<213> ORGANISM: Artificial Sequence
<220> FEATURE:
<223> OTHER INFORMATION: primer LysA-1

<400> SEQUENCE: 22
gcggatcctc catgccaaaa tgatcccgga tgctga                               36

<210> SEQ ID NO 23
<211> LENGTH: 47
<212> TYPE: DNA
<213> ORGANISM: Artificial Sequence
<220> FEATURE:
<223> OTHER INFORMATION: primer LysA-2

<400> SEQUENCE: 23
gacaaaagcc cggacaccag aaatgccaca ttcactgttc agcaccg                   47

<210> SEQ ID NO 24
<211> LENGTH: 38
<212> TYPE: DNA
<213> ORGANISM: Artificial Sequence
<220> FEATURE:
<223> OTHER INFORMATION: primer LysA-3

<400> SEQUENCE: 24
gcggatccgg tatggtgctg atcaaccgta tcctgcct                             38

<210> SEQ ID NO 25
<211> LENGTH: 28
<212> TYPE: DNA
<213> ORGANISM: Artificial Sequence
<220> FEATURE:

```
<223> OTHER INFORMATION: primer LysA-4

<400> SEQUENCE: 25
gaaagcttgc gcagtgtttt gcctgtgt                                              28

<210> SEQ ID NO 26
<211> LENGTH: 36
<212> TYPE: DNA
<213> ORGANISM: Artificial Sequence
<220> FEATURE:
<223> OTHER INFORMATION: primer phoAp-1

<400> SEQUENCE: 26
gcaagcttat gcggtgagtt ttttctctt aattat                                      36

<210> SEQ ID NO 27
<211> LENGTH: 46
<212> TYPE: DNA
<213> ORGANISM: Artificial Sequence
<220> FEATURE:
<223> OTHER INFORMATION: primer phoAp-2

<400> SEQUENCE: 27
cggtgctgaa cagtgaatgt ggcatttctg gtgtccgggc ttttgt                          46

<210> SEQ ID NO 28
<211> LENGTH: 1263
<212> TYPE: DNA
<213> ORGANISM: Escherichia coli
<220> FEATURE:
<221> NAME/KEY: CDS
<222> LOCATION: (1)..(1263)

<400> SEQUENCE: 28
```

| | | | | | | | | | | | | | | | | |
|---|---|---|---|---|---|---|---|---|---|---|---|---|---|---|---|---|
| atg | cca | cat | tca | ctg | ttc | agc | acc | gat | acc | gat | ctc | acc | gcc | gaa | aat | 48 |
| Met | Pro | His | Ser | Leu | Phe | Ser | Thr | Asp | Thr | Asp | Leu | Thr | Ala | Glu | Asn | |
| 1 | | | | 5 | | | | | 10 | | | | | 15 | | |

| ctg | ctg | cgt | ttg | ccc | gct | gaa | ttt | ggc | tgc | ccg | gtg | tgg | gtc | tac | gat | 96 |
|---|---|---|---|---|---|---|---|---|---|---|---|---|---|---|---|---|
| Leu | Leu | Arg | Leu | Pro | Ala | Glu | Phe | Gly | Cys | Pro | Val | Trp | Val | Tyr | Asp | |
| | | | 20 | | | | | 25 | | | | | 30 | | | |

| gcg | caa | att | att | cgt | cgg | cag | att | gca | gcg | ctg | aaa | cag | ttt | gat | gtg | 144 |
|---|---|---|---|---|---|---|---|---|---|---|---|---|---|---|---|---|
| Ala | Gln | Ile | Ile | Arg | Arg | Gln | Ile | Ala | Ala | Leu | Lys | Gln | Phe | Asp | Val | |
| | | 35 | | | | | 40 | | | | | 45 | | | | |

| gtg | cgc | ttt | gca | cag | aaa | gcc | tgt | tcc | aat | att | cat | att | ttg | cgc | tta | 192 |
|---|---|---|---|---|---|---|---|---|---|---|---|---|---|---|---|---|
| Val | Arg | Phe | Ala | Gln | Lys | Ala | Cys | Ser | Asn | Ile | His | Ile | Leu | Arg | Leu | |
| 50 | | | | | 55 | | | | | 60 | | | | | | |

| atg | cgt | gag | cag | ggc | gtg | aaa | gtg | gat | tcc | gtc | tcg | tta | ggc | gaa | ata | 240 |
|---|---|---|---|---|---|---|---|---|---|---|---|---|---|---|---|---|
| Met | Arg | Glu | Gln | Gly | Val | Lys | Val | Asp | Ser | Val | Ser | Leu | Gly | Glu | Ile | |
| 65 | | | | 70 | | | | | 75 | | | | | 80 | | |

| gag | cgt | gcg | ttg | gcg | gcg | ggt | tac | aat | ccg | caa | acg | cac | ccc | gat | gat | 288 |
|---|---|---|---|---|---|---|---|---|---|---|---|---|---|---|---|---|
| Glu | Arg | Ala | Leu | Ala | Ala | Gly | Tyr | Asn | Pro | Gln | Thr | His | Pro | Asp | Asp | |
| | | | | 85 | | | | | 90 | | | | | 95 | | |

| att | gtt | ttt | acg | gca | gat | gtt | atc | gat | cag | gcg | acg | ctt | gaa | cgc | gtc | 336 |
|---|---|---|---|---|---|---|---|---|---|---|---|---|---|---|---|---|
| Ile | Val | Phe | Thr | Ala | Asp | Val | Ile | Asp | Gln | Ala | Thr | Leu | Glu | Arg | Val | |
| | | | 100 | | | | | 105 | | | | | 110 | | | |

| agt | gaa | ttg | caa | att | ccg | gtg | aat | gcg | ggt | tct | gtt | gat | atg | ctc | gac | 384 |
|---|---|---|---|---|---|---|---|---|---|---|---|---|---|---|---|---|
| Ser | Glu | Leu | Gln | Ile | Pro | Val | Asn | Ala | Gly | Ser | Val | Asp | Met | Leu | Asp | |
| | | 115 | | | | | 120 | | | | | 125 | | | | |

| caa | ctg | ggc | cag | gtt | tcg | cca | ggg | cat | cgg | gta | tgg | ctg | cgc | gtt | aat | 432 |
|---|---|---|---|---|---|---|---|---|---|---|---|---|---|---|---|---|
| Gln | Leu | Gly | Gln | Val | Ser | Pro | Gly | His | Arg | Val | Trp | Leu | Arg | Val | Asn | |
| 130 | | | | | 135 | | | | | 140 | | | | | | |

| ccg | ggg | ttt | ggt | cac | gga | cat | agc | caa | aaa | acc | aat | acc | ggt | ggc | gaa | 480 |
|---|---|---|---|---|---|---|---|---|---|---|---|---|---|---|---|---|
| Pro | Gly | Phe | Gly | His | Gly | His | Ser | Gln | Lys | Thr | Asn | Thr | Gly | Gly | Glu | |
| 145 | | | | 150 | | | | | 155 | | | | | 160 | | |

```
aac agc aag cac ggt atc tgg tac acc gat ctg ccc gcc gca ctg gac      528
Asn Ser Lys His Gly Ile Trp Tyr Thr Asp Leu Pro Ala Ala Leu Asp
            165                 170                 175 gtg ata caa cgt cat cat ctg cag ctg gtc ggc att cac atg cac att      576
Val Ile Gln Arg His His Leu Gln Leu Val Gly Ile His Met His Ile
        180                 185                 190 ggt tct ggc gtt gat tat gcc cat ctg gaa cag gtg tgt ggt gct atg      624
Gly Ser Gly Val Asp Tyr Ala His Leu Glu Gln Val Cys Gly Ala Met
    195                 200                 205 gtg cgt cag gtc atc gaa ttc ggt cag gat tta cag gct att tct gcg      672
Val Arg Gln Val Ile Glu Phe Gly Gln Asp Leu Gln Ala Ile Ser Ala
210                 215                 220 ggc ggt ggg ctt tct gtt cct tat caa cag ggt gaa gag gcg gtt gat      720
Gly Gly Gly Leu Ser Val Pro Tyr Gln Gln Gly Glu Glu Ala Val Asp
225                 230                 235                 240 acc gaa cat tat tat ggt ctg tgg aat gcc gcg cgt gag caa atc gcc      768
Thr Glu His Tyr Tyr Gly Leu Trp Asn Ala Ala Arg Glu Gln Ile Ala
                245                 250                 255 cgc cat ttg ggc cac cct gtg aaa ctg gaa att gaa ccg ggt cgc ttc      816
Arg His Leu Gly His Pro Val Lys Leu Glu Ile Glu Pro Gly Arg Phe
            260                 265                 270 ctg gta gcg cag tct ggc gta tta att act cag gtg cgg agc gtc aaa      864
Leu Val Ala Gln Ser Gly Val Leu Ile Thr Gln Val Arg Ser Val Lys
        275                 280                 285 caa atg ggg agc cgc cac ttt gtg ctg gtt gat gcc ggg ttc aac gat      912
Gln Met Gly Ser Arg His Phe Val Leu Val Asp Ala Gly Phe Asn Asp
    290                 295                 300 ctg atg cgc ccg gca atg tac ggt agt tac cac cat atc agt gcc ctg      960
Leu Met Arg Pro Ala Met Tyr Gly Ser Tyr His His Ile Ser Ala Leu
305                 310                 315                 320 gca gct gat ggt cgt tct ctg gaa cac gcg cca acg gtg gaa acc gtc     1008
Ala Ala Asp Gly Arg Ser Leu Glu His Ala Pro Thr Val Glu Thr Val
                325                 330                 335 gtc gcc gga ccg tta tgt gaa tcg ggc gat gtc ttt acc cag cag gaa     1056
Val Ala Gly Pro Leu Cys Glu Ser Gly Asp Val Phe Thr Gln Gln Glu
            340                 345                 350 ggg gga aat gtt gaa acc cgc gcc ttg ccg gaa gtg aag gca ggt gat     1104
Gly Gly Asn Val Glu Thr Arg Ala Leu Pro Glu Val Lys Ala Gly Asp
        355                 360                 365 tat ctg gta ctg cat gat aca ggg gca tat ggc gca tca atg tca tcc     1152
Tyr Leu Val Leu His Asp Thr Gly Ala Tyr Gly Ala Ser Met Ser Ser
    370                 375                 380 aac tac aat agc cgt ccg ctg tta cca gaa gtt ctg ttt gat aat ggt     1200
Asn Tyr Asn Ser Arg Pro Leu Leu Pro Glu Val Leu Phe Asp Asn Gly
385                 390                 395                 400 cag gcg cgg ttg att cgc cgt cgc cag acc atc gaa gaa tta ctg gcg     1248
Gln Ala Arg Leu Ile Arg Arg Arg Gln Thr Ile Glu Glu Leu Leu Ala
                405                 410                 415 ctg gaa ttg ctt taa                                                 1263
Leu Glu Leu Leu
            420

<210> SEQ ID NO 29
<211> LENGTH: 420
<212> TYPE: PRT
<213> ORGANISM: Escherichia coli

<400> SEQUENCE: 29

Met Pro His Ser Leu Phe Ser Thr Asp Thr Asp Leu Thr Ala Glu Asn
1               5                   10                  15
```

```
Leu Leu Arg Leu Pro Ala Glu Phe Gly Cys Pro Val Trp Val Tyr Asp
             20                  25                  30

Ala Gln Ile Ile Arg Arg Gln Ile Ala Ala Leu Lys Gln Phe Asp Val
         35                  40                  45

Val Arg Phe Ala Gln Lys Ala Cys Ser Asn Ile His Ile Leu Arg Leu
 50                  55                  60

Met Arg Glu Gln Gly Val Lys Val Asp Ser Val Ser Leu Gly Glu Ile
 65                  70                  75                  80

Glu Arg Ala Leu Ala Ala Gly Tyr Asn Pro Gln Thr His Pro Asp Asp
                 85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
            115                 120                 125

Gln Leu Gly Gln Val Ser Pro Gly His Arg Val Trp Leu Arg Val Asn
        130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His Leu Gln Leu Val Gly Ile His Met His Ile
            180                 185                 190

Gly Ser Gly Val Asp Tyr Ala His Leu Glu Gln Val Cys Gly Ala Met
        195                 200                 205

Val Arg Gln Val Ile Glu Phe Gly Gln Asp Leu Gln Ala Ile Ser Ala
    210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
            420

<210> SEQ ID NO 30
```

<211> LENGTH: 5218
<212> TYPE: DNA
<213> ORGANISM: Artificial Sequence
<220> FEATURE:
<223> OTHER INFORMATION: fragment MUD-aroG4-pheAB-aroL

<400> SEQUENCE: 30

```
gtattgattc acttgaagta cgaaaaaaac cgggaggaca ttggattatt cgggatctga      60
tgggattaga tttggtgggg cttgcaagcc tgtagtgcaa attttagtcg ttaatcaatg     120
aaacgcgaaa gatagtaaaa aattgcaaaa agagtttgta gaaacgcaaa aaggccatcc     180
gtcaggatgg ccttctgctt aatttgatgc ctggcagttt atggcgggcg tcctgcccgc     240
caccctccgg gccgttgctt cgcaacgttc aaatccgctc ccggcggatt tgtcctactc     300
aggagagcgt tcaccgacaa acaacagata aaacgaaagg cccagtcttt cgactgagcc     360
tttcgtttta tttgatgcct ggcagttccc tactctcgca tggggagacc ccacactacc     420
atcggcgcta cggcgtttca cttctgagtt cggcatgggg tcaggtggga ccaccgcgct     480
actgccgcca ggcaaaggat ctaagctttc tagacgctca agttagtata aaaaagcagg     540
cttcaacttc ggacgaaaaa atatgattga actcgcatca acaattgatc gtctgtgcca     600
gggcgctgcg aatttcagaa atcacctggc tgggttcgtt tgttgcgtcg atgataatat     660
gcgcaacttc gcgatatagc gcatcgcgtt cttccagcac ttcctgaact tcttcgctca     720
gcggttttcc cgttaaggtt ggccgtaaat cttcttccgg tgcagcttgc agtcggttaa     780
ccaggactga tactgcgcca cacaaataaa ccacgatccc gttattttgc atgaagtgac     840
gattaaattc cgtcagaata atgccgccgc ctgtagcgat aacggtggat ggcgcagtta     900
ccgcttccag cgccgccgtt tctctggcgc gaaatcccgc ccactcttcc ctttcgacga     960
tctccgcgac cgtcatattg agctgtgatt gcaaccactg atcggtatcg acaaaccgac    1020
ggttaagcga atcggcaagg gccattccga ccgttgtttt accacagccc cgaggcccga    1080
tcagaaaaag aggttgtgtc atcgtgggtt ttccccaata ggtcgcaatg cggcgaaagc    1140
cggtgtcatg agaatagcga tcataccatc aaactagtac aatttcgatt gtaaagaaaa    1200
aattccactt aaagtgaaaa tctcaataca ccccttacta taccaataaa tattcaagaa    1260
tgaagtgtaa ataataaatt acatttagcc acgactacgt tgcacttcca gccaccactt    1320
ctcgagctcg gtacccactc cgccggaact gactaaagat gatgagcgtt atccgggtca    1380
cgatccgcgt tacgcgaaac tgagcgagaa agaactgccg ctgacggaaa gcctggcgct    1440
gaccattgac cgcgtgatcc cttactggaa tgaaactatt ctgccgcgta tgaagagcgg    1500
tgagcgcgtg atcatcgctg cacacggtaa ctctttacgt gcgctggtga atatcttga    1560
taacatgagc gaagaagaga ttcttgagct taatatcccg actggcgtgc cgctggtgta    1620
tgagttcgac gagaatttca aaccgctgaa acgctattat ctgggtaatg ctgacgagat    1680
cgcagcgaaa gcagcggcgg ttgcaaacca gggtaaagcg aagtaaacgt cattcgttta    1740
aaatgagaaa gccgactgca agtgagtcgg ctttttgtt gctaacaatg gagcacattg    1800
cctgatgcga cgctgcgcga cttatcaggc ctgtggtgat tcatcggata cgccactctg    1860
acggcgcatc cgacaattaa accttacccg cgacgcgctt ttactgcatt cgccagttga    1920
cgtaacagag catcggtatc ttcccagccg atgcaggcat cggtgatgct cttaccgtag    1980
gccagcggct ccccgctctc gaggctctga ttgccttcca ccagatggct ttccaccatc    2040
acgccaataa tggcctttc gccaccggca atctgctggc aaacgtcagc acaaacatcc    2100
atctgctttt tgaattgttt ggacgagtta gcatggctga aatcgatcat cacctgtgct    2160
```

-continued

```
ggcaggcctg ctttgttcag cccttctttc acttcagcaa cgtgcttcgc gctgtagtta   2220
ggctctttac cgccgcgcag aatgatatgg caatcgccgt taccgctggt attcacaatc   2280
gccgaatgcc cccatttcgt tacggacagg aagcagtgcg gcgcaccggc ggcattaatg   2340
gcatcgatag ccactttaat cgtaccgtcg gtgccatttt tgaagccgac cggacaagaa   2400
agccctgatg ccagttcgcg gtgcacctgc gattcggtgg tacgtgcgcc aattgcgccc   2460
cagctcatca ggtcagcgag atattgtagg gtgatcatat cgagaaactc acctgccgct   2520
ggcagaccgc tgtcgttaat atcaagcagc aatttacggg ctatacgcag accgtcgttg   2580
atctggaagc tattatccat atgcggatcg ttaatcagcc cttccagcc caccgtggta    2640
cgcggctttt caaaatagac gcgcattacg atttccagct catctttcag ctcttcacgc   2700
agcgccagca agcgagtggc atactctttt gccgcgacag gatcatgaat tgagcatggg   2760
ccaatcacaa ccaacaggcg atcatcatta cctttcagga tcttatggat cgcttttcgg   2820
gcatgggcaa ccgtattcgc ggcattttca gtagcgggga attttccag caatgcgaca    2880
ggaggaagta actctttgat ttctttgatg cgtaaatcgt cgttctgata attcatgtct   2940
gttccagtgt tgccatactt atcttagtga atgcaatact tccaatctat atcttccgtc   3000
agaatgtgta aacggggttt tacactatga acggattaat cctggaatta gcaagaaaaa   3060
cgccagattg tcgcgaaaaa cgagatctct cctacaattt ctaactgtaa ctcctttgtt   3120
tgttaattat ttcaagattc tctgctgcgt ttcataacct ggctgaaatc ttaaaccaat   3180
gccttatatt cacctgcaaa tgcactgttg gaagaggtta tccgacataa cgaccataac   3240
aggagcatcc tatgaaaatg acaaaactgg ccacattatt tctgactgcc actctaagcc   3300
ttgccagcgg tgccgcactg gctgccgata gcggagcgca aactaataac ggccaggcaa   3360
acgccgcagc tgatgcgggc caggtagccc ctgacgcccg tgaaaatgtc gcgccaaata   3420
acgtcgacct gcaggcatgc aagcttgcat gcctgcagca caaaggcgaa gcacgtcgtg   3480
ccgcaacatc ggtgaaagac gccaacttcg tcgaagaagt tgaagaagag tagtccttta   3540
tattgagtgt atcgccaacg cgccttcggg cgcgtttttt gttgacagcg tgaaaacagt   3600
acgggtactg tactaaagtc acttaacctc ccaaatcggg gggccttttt tattgataac   3660
aaaaaggcaa cactatgaca tcggaaaacc cgttactggc gctgcgagag aaaatcagcg   3720
cgctggatga aaaattatta gcgttactgg cagaacggcg cgaactggcc gtcgaggtgg   3780
gaaaagccaa actgctctcg catcgcccgg tacgtgatat tgatcgtgaa cgcgatttgc   3840
tggaaagatt aattacgctc ggtaaagcgc accatctgga cgcccattac attactcgcc   3900
tgttccagct catcattgaa gattccgtat aactcagca ggctttgctc caacaacatc    3960
tcaataaaat taatccgcac tcagcacgca tcgcttttct cggccccaaa ggttcttatt   4020
cccatcttgc ggcgcgccag tatgctgccc gtcactttga gcaattcatt gaaagtggct   4080
gcgccaaatt tgccgatatt tttaatcagg tggaaccgg ccaggccgac tatgccgtcg    4140
taccgattga aaataccagc tccggtgcca taaacgacgt ttacgatctg ctgcaacata   4200
ccagcttgtc gattgttggc gagatgacgt taactatcga ccattgtttg ttggtctccg   4260
gcactactga tttatccacc atcaatacgg tctacagcca tccgcagcca ttccagcaat   4320
gcagcaaatt ccttaatcgt tatccgcact ggaagattga atataccgaa agtacgtctg   4380
cggcaatgga aaaggttgca caggcaaaat caccgcatgt tgctgcgttg ggaagcgaag   4440
ctggcggcac tttgtacggt ttgcaggtac tggagcgtat tgaagcaaat cagcgacaaa   4500
acttcacccg atttgtggtg ttggcgcgta aagccattaa cgtgtctgat caggttccgg   4560
```

-continued

```
cgaaaaccac gttgttaatg gcgaccgggc aacaagccgg tgcgctggtt gaagcgttgc    4620
tggtactgcg caaccacaat ctgattatga cccgtctgga accacgcccg attcacggta    4680
atccatggga agagatgttc tatctggata ttcaggccaa tcttgaatca gcggaaatgc    4740
aaaaagcatt gaaagagtta ggggaaatca cccgttcaat gaaggtattg ggctgttacc    4800
caagtgagaa cgtagtgcct gttgatccaa cctgatgaaa aggtgccgga tgatgtgaat    4860
catccggcac tggattatta ctggcgattg tcattcgcct gacgcaataa cacgcggctt    4920
tcactctgaa aacgctgtgc gtaatcgccg aaccagtgct ccaccttgcg gaaactgtca    4980
ataaacgcct gcttatcgcc ctgctccagc aactcaatcg cctcgccgaa acgcttatag    5040
taacgtttga ttaacgccag attacgctct gacgacataa tgatgtcggc ataaagctgc    5100
ggatccccat gtaatgaata aaaagcagta attaatacat ctgtttcatt tgaagcgcga    5160
aagctaaagt tttcgcattt atcgtgaaac gctttcgcgt ttttcgtgcg ccgcttca      5218
```

<210> SEQ ID NO 31
<211> LENGTH: 42
<212> TYPE: DNA
<213> ORGANISM: Artificial Sequence
<220> FEATURE:
<223> OTHER INFORMATION: primer

<400> SEQUENCE: 31

```
taaacaagat ctcagtaaaa agttaatctt ttcaacagct gt                        42
```

<210> SEQ ID NO 32
<211> LENGTH: 69
<212> TYPE: DNA
<213> ORGANISM: Artificial Sequence
<220> FEATURE:
<223> OTHER INFORMATION: primer

<400> SEQUENCE: 32

```
ttctttgatg cgtaaatcgt cgttctgata attcatttta ttttctccat gtacaaatac    60
attaaaaaa                                                              69
```

<210> SEQ ID NO 33
<211> LENGTH: 40
<212> TYPE: DNA
<213> ORGANISM: Artificial Sequence
<220> FEATURE:
<223> OTHER INFORMATION: primer

<400> SEQUENCE: 33

```
ctagtaagat cttgaagcct gctttttat actaagttgg                            40
```

<210> SEQ ID NO 34
<211> LENGTH: 63
<212> TYPE: DNA
<213> ORGANISM: Artificial Sequence
<220> FEATURE:
<223> OTHER INFORMATION: primer

<400> SEQUENCE: 34

```
ccgatgttgc ggcacgacgt gcttcgcctt tgtgctcgct caagttagta taaaaagct     60 gaa                                                                    63
```

<210> SEQ ID NO 35
<211> LENGTH: 4842
<212> TYPE: DNA
<213> ORGANISM: Artificial Sequence
<220> FEATURE:

<223> OTHER INFORMATION: fragment MUD-(PPhoA-aroG4)-pheAB-aroL

<400> SEQUENCE: 35

```
tgtattgatt cacttgaagt acgaaaaaaa ccgggaggac attggattat tcgggatctg      60
atgggattag atttggtggg gcttgcaagc ctgtagtgca aattttagtc gttaatcaat     120
gaaacgcgaa agatagtaaa aaattgcaaa aagagtttgt agaaacgcaa aaaggccatc     180
cgtcaggatg gccttctgct taatttgatg cctggcagtt tatggcgggc gtcctgcccg     240
ccaccctccg ggccgttgct tcgcaacgtt caaatccgct cccggcggat ttgtcctact     300
caggagagcg ttcaccgaca aacaacagat aaaacgaaag gcccagtctt tcgactgagc     360
cttttcgtttt atttgatgcc tggcagttcc ctactctcgc atggggagac cccacactac     420
catcggcgct acggcgtttc acttctgagt tcggcatggg gtcaggtggg accaccgcgc     480
tactgccgcc aggcaaagga tctaagcttt ctagacgctc aagttagtat aaaaaagcag     540
gcttcaactt cggacgaaaa aatatgattg aactcgcatc aacaattgat cgtctgtgcc     600
agggcgctgc gaatttcaga atcacctggc tgggttcgt tgttgcgtc gatgataata      660
tgcgcaactt cgcgatatag cgcatcgcgt tcttccagca cttcctgaac ttcttcgctc     720
agcggttttc ccgttaaggt tggccgtaaa tcttcttccg gtgcagcttg cagtcggtta     780
accaggactg atactggcgc acacaaataa accacgatcc cgttattttg catgaagtga     840
cgattaaatt ccgtcagaat aatgccgccg cctgtagcga taacggtgga tggcgcagtt     900
accgcttcca gcgccgccgt ttctctggcg cgaaatcccg cccactcttc cctttcgacg     960
atctccgcga ccgtcatatt gagctgtgat tgcaaccact gatcggtatc gacaaaccga    1020
cggttaagcg aatcggcaag ggccattccg accgttgttt taccacagcc ccgaggcccg    1080
atcagaaaaa gaggttgtgt catcgtgggt tttccccaat aggtcgcaat gcggcgaaag    1140
ccggtgtcat gagaatagcg atcataccat caaactagta caatttcgat tgtaaagaaa    1200
aaattccact taaagtgaaa atctcaatac accccttact ataccaataa atattcaaga    1260
atgaagtgta aataataaat tacatttagc cacgactacg ttgcacttcc agccaccact    1320
tctcgagctc ggtacccact ccgccggaac tgactaaaga tgatgagcgt tatccgggtc    1380
acgatccgcg ttacgcgaaa ctgagcgaga agaactgcc gctgacggaa agcctggcgc     1440
tgaccattga ccgcgtgatc ccttactgga atgaaactat tctgccgcgt atgaagagcg    1500
gtgagcgcgt gatcatcgct gcacacggta actctttacg tgcgctggtg aaatatcttg    1560
ataacatgag cgaagaagag attcttgagc ttaatatccc gactggcgtg ccgctggtgt    1620
atgagttcga cgagaatttc aaaccgctga acgctatta tctgggtaat gctgacgaga     1680
tcgcagcgaa agcagcggcg gttgcaaacc agggtaaagc gaagtaaacg tcattcgttt    1740
aaaatgagaa agccgactgc aagtgagtcg gcttttttgt tgctaacaat ggagcacatt    1800
gcctgatgcg acgctgcgcg acttatcagg cctgtggtga ttcatcggat acgccactct    1860
gacggcgcat ccgacaatta aaccttaccc gcgacgcgct tttactgcat tcgccagttg    1920
acgtaacaga gcatcggtat cttcccagcc gatgcaggca tcgtgatgc tcttaccgta     1980
ggccagcggc tccccgctct cgaggctctg attgccttcc accagatggc tttccaccat    2040
cacgccaata atggcctttt cgccaccggc aatctgctgg caaacgtcag cacaaacatc    2100
catctgcttt ttgaattgtt tggacgagtt agcatggctg aaatcgatca tcacctgtgc    2160
tggcaggcct gctttgttca gcccttcttt cacttcagca acgtgcttcg cgctgtagtt    2220
aggctcttta ccgccgcgca gaatgatatg gcaatcgccg ttaccgctgg tattcacaat    2280
```

```
cgccgaatgc ccccatttcg ttacggacag gaagcagtgc ggcgcaccgg cggcattaat    2340
ggcatcgata gccactttaa tcgtaccgtc ggtgccattt ttgaagccga ccggacaaga    2400
aagccctgat gccagttcgc ggtgcacctg cgattcggtg gtacgtgcgc caattgcgcc    2460
ccagctcatc aggtcagcga gatattgtag ggtgatcata tcgagaaact cacctgccgc    2520
tggcagaccg ctgtcgttaa tatcaagcag caatttacgg gctatacgca gaccgtcgtt    2580
gatctggaag ctattatcca tatgcggatc gttaatcagc cctttccagc ccaccgtggt    2640
acgcggcttt tcaaaataga cgcgcattac gatttccagc tcatctttca gctcttcacg    2700
cagcgccagc aagcgagtgg catactcttt tgccgcgaca ggatcatgaa ttgagcatgg    2760
gccaatcaca accaacaggc gatcatcatt accttcagg atcttatgga tcgcttttcg    2820
ggcatgggca accgtattcg cggcatttc agtagcgggg aattttcca gcaatgcgac    2880 aggaggaagt aactctttga tttctttgat gcgtaaatcg tcgttctgat aattcatttt    2940
attttctcca tgtacaaata cattaaaaaa taaaaacaaa gcgactataa gtctcggccg    3000
tgacaacttt atgacagctg ttgaaaagat taacttttta ctgagatctt gaagcctgct    3060
tttttatact aacttgagcg agcacaaagg cgaagcacgt cgtgccgcaa catcggtgaa    3120
agacgccaac ttcgtcgaag aagttgaaga agagtagtcc tttatattga gtgtatcgcc    3180
aacgcgccct cgggcgcgtt ttttgttgac agcgtgaaaa cagtacgggt actgtactaa    3240
agtcacttaa cctcccaaat cgggggggcct tttttattga taacaaaaag gcaacactat    3300
gacatcggaa aacccgttac tggcgctgcg agagaaaatc agcgcgctgg atgaaaaatt    3360
attagcgtta ctggcagaac ggcgcgaact ggccgtcgag gtgggaaaag ccaaactgct    3420
ctcgcatcgc ccggtacgtg atattgatcg tgaacgcgat ttgctggaaa gattaattac    3480
gctcggtaaa gcgcaccatc tggacgccca ttacattact cgcctgttcc agctcatcat    3540
tgaagattcc gtattaactc agcaggcttt gctccaacaa catctcaata aaattaatcc    3600
gcactcagca cgcatcgctt ttctcggccc caaaggttct tattcccatc ttgcggcgcg    3660
ccagtatgct gcccgtcact ttgagcaatt cattgaaagt ggctgcgcca aattgccga    3720 tatttttaat caggtggaaa ccggccaggc cgactatgcc gtcgtaccga ttgaaaatac    3780
cagctccggt gccataaacg acgtttacga tctgctgcaa cataccagct tgtcgattgt    3840
tggcgagatg acgttaacta tcgaccattg tttgttggtc tccggcacta ctgatttatc    3900
caccatcaat acggtctaca gccatccgca gccattccag caatgcagca aattccttaa    3960
tcgttatccg cactggaaga ttgaatatac cgaaagtacg tctgcggcaa tggaaaaggt    4020
tgcacaggca aaatcaccgc atgttgctgc gttgggaagc gaagctggcg gcactttgta    4080
cggtttgcag gtactggagc gtattgaagc aaatcagcga caaaacttca cccgatttgt    4140
ggtgttggcg cgtaaagcca ttaacgtgtc tgatcaggtt ccggcgaaaa ccacgttgtt    4200
aatggcgacc gggcaacaag ccggtgcgct ggttgaagcg ttgctggtac tgcgcaacca    4260
caatctgatt atgacccgtc tggaaccacg cccgattcac ggtaatccat gggaagagat    4320
gttctatctg gatattcagg ccaatcttga atcagcggaa atgcaaaaag cattgaaaga    4380 gttagggaa atcacccgtt caatgaaggt attgggctgt tacccaagtg agaacgtagt    4440
gcctgttgat ccaacctgat gaaaaggtgc cggatgatgt gaatcatccg gcactggatt    4500
attactggcg attgtcattc gcctgacgca ataacacgcg gctttcactc tgaaaacgct    4560
gtgcgtaatc gccgaaccag tgctccacct tgcggaaact gtcaataaac gcctgcttat    4620
cgccctgctc cagcaactca atcgcctcgc cgaaacgctt atagtaacgt ttgattaacg    4680
```

```
                                          -continued ccagattacg ctctgacgac ataatgatgt cggcataaag ctgcggatcc ccatgtaatg      4740
aataaaaagc agtaattaat acatctgttt catttgaagc gcgaaagcta agttttcgc       4800 atttatcgtg aaacgctttc gcgttttcg tgcgccgctt ca                          4842

<210> SEQ ID NO 36
<211> LENGTH: 1053
<212> TYPE: DNA
<213> ORGANISM: Eschericha coli
<220> FEATURE:
<221> NAME/KEY: CDS
<222> LOCATION: (1)..(1053)

<400> SEQUENCE: 36 atg aat tat cag aac gac gat tta cgc atc aaa gaa atc aaa gag tta        48
Met Asn Tyr Gln Asn Asp Asp Leu Arg Ile Lys Glu Ile Lys Glu Leu
1               5                   10                  15 ctt cct cct gtc gca ttg ctg gaa aaa ttc ccc gct act gaa aat gcc        96
Leu Pro Pro Val Ala Leu Leu Glu Lys Phe Pro Ala Thr Glu Asn Ala
            20                  25                  30 gcg aat acg gtt gcc cat gcc cga aaa gcg atc cat aag atc ctg aaa       144
Ala Asn Thr Val Ala His Ala Arg Lys Ala Ile His Lys Ile Leu Lys
        35                  40                  45 ggt aat gat gat cgc ctg ttg gtt gtg att ggc cca tgc tca att cat       192
Gly Asn Asp Asp Arg Leu Leu Val Val Ile Gly Pro Cys Ser Ile His
    50                  55                  60 gat cct gtc gcg gca aaa gag tat gcc act cgc ttg ctg gcg ctg cgt       240
Asp Pro Val Ala Ala Lys Glu Tyr Ala Thr Arg Leu Leu Ala Leu Arg
65                  70                  75                  80 gaa gag ctg aaa gat gag ctg gaa atc gta atg cgc gtc tat ttt gaa       288
Glu Glu Leu Lys Asp Glu Leu Glu Ile Val Met Arg Val Tyr Phe Glu
                85                  90                  95 aag ccg cgt acc acg gtg ggc tgg aaa ggg ctg att aac gat ccg cat       336
Lys Pro Arg Thr Thr Val Gly Trp Lys Gly Leu Ile Asn Asp Pro His
            100                 105                 110 atg gat aat agc ttc cag atc aac gac ggt ctg cgt ata gcc cgt aaa       384
Met Asp Asn Ser Phe Gln Ile Asn Asp Gly Leu Arg Ile Ala Arg Lys
        115                 120                 125 ttg ctg ctt gat att aac gac agc ggt ctg cca gcg gca ggt gag ttt       432
Leu Leu Leu Asp Ile Asn Asp Ser Gly Leu Pro Ala Ala Gly Glu Phe
    130                 135                 140 ctc gat atg atc acc cca caa tat ctc gct gac ctg atg agc tgg ggc       480
Leu Asp Met Ile Thr Pro Gln Tyr Leu Ala Asp Leu Met Ser Trp Gly
145                 150                 155                 160 gca att ggc gca cgt acc acc gaa tcg cag gtg cac cgc gaa ctg gca       528
Ala Ile Gly Ala Arg Thr Thr Glu Ser Gln Val His Arg Glu Leu Ala
                165                 170                 175 tca ggg ctt tct tgt ccg gtc ggc ttc aaa aat ggc acc gac ggt acg       576
Ser Gly Leu Ser Cys Pro Val Gly Phe Lys Asn Gly Thr Asp Gly Thr
            180                 185                 190 att aaa gtg gct atc gat gcc att aat gcc gcc ggt gcg ccg cac tgc       624
Ile Lys Val Ala Ile Asp Ala Ile Asn Ala Ala Gly Ala Pro His Cys
        195                 200                 205 ttc ctg tcc gta acg aaa tgg ggg cat tcg gcg att gtg aat acc agc       672
Phe Leu Ser Val Thr Lys Trp Gly His Ser Ala Ile Val Asn Thr Ser
    210                 215                 220 ggt aac ggc gat tgc cat atc att ctg cgc ggc ggt aaa gag cct aac       720
Gly Asn Gly Asp Cys His Ile Ile Leu Arg Gly Gly Lys Glu Pro Asn
225                 230                 235                 240 tac agc gcg aag cac gtt gct gaa gtg aaa gaa ggg ctg aac aaa gca       768
Tyr Ser Ala Lys His Val Ala Glu Val Lys Glu Gly Leu Asn Lys Ala
                245                 250                 255
```

```
ggc ctg cca gca cag gtg atg atc gat ttc agc cat gct aac tcg tcc         816
Gly Leu Pro Ala Gln Val Met Ile Asp Phe Ser His Ala Asn Ser Ser
        260                 265                 270 aaa caa ttc aaa aag cag atg gat gtt tgt gct gac gtt tgc cag cag         864
Lys Gln Phe Lys Lys Gln Met Asp Val Cys Ala Asp Val Cys Gln Gln
            275                 280                 285 att gcc ggt ggc gaa aag gcc att att ggc gtg atg gtg gaa agc cat         912
Ile Ala Gly Gly Glu Lys Ala Ile Ile Gly Val Met Val Glu Ser His
290                 295                 300 ctg gtg gaa ggc aat cag agc ctc gag agc ggg gag ccg ctg gcc tac         960
Leu Val Glu Gly Asn Gln Ser Leu Glu Ser Gly Glu Pro Leu Ala Tyr
305                 310                 315                 320 ggt aag agc atc acc gat gcc tgc atc ggc tgg gaa gat acc gat gct        1008
Gly Lys Ser Ile Thr Asp Ala Cys Ile Gly Trp Glu Asp Thr Asp Ala
                325                 330                 335 ctg tta cgt caa ctg gcg aat gca gta aaa gcg cgt cgc ggg taa            1053
Leu Leu Arg Gln Leu Ala Asn Ala Val Lys Ala Arg Arg Gly
                340                 345                 350

<210> SEQ ID NO 37
<211> LENGTH: 350
<212> TYPE: PRT
<213> ORGANISM: Eschericha coli

<400> SEQUENCE: 37

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Gly Glu Phe
    130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255
```

```
Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
        290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
                340                 345                 350

<210> SEQ ID NO 38
<211> LENGTH: 525
<212> TYPE: DNA
<213> ORGANISM: Eschericha coli
<220> FEATURE:
<221> NAME/KEY: CDS
<222> LOCATION: (1)..(525)

<400> SEQUENCE: 38 atg aca caa cct ctt ttt ctg atc ggg cct cgg ggc tgt ggt aaa aca       48
Met Thr Gln Pro Leu Phe Leu Ile Gly Pro Arg Gly Cys Gly Lys Thr
1               5                   10                  15 acg gtc gga atg gcc ctt gcc gat tcg ctt aac cgt cgg ttt gtc gat       96
Thr Val Gly Met Ala Leu Ala Asp Ser Leu Asn Arg Arg Phe Val Asp
                20                  25                  30 acc gat cag tgg ttg caa tca cag ctc aat atg acg gtc gcg gag atc      144
Thr Asp Gln Trp Leu Gln Ser Gln Leu Asn Met Thr Val Ala Glu Ile
            35                  40                  45 gtc gaa agg gaa gag tgg gcg gga ttt cgc gcc aga gaa acg gcg gcg      192
Val Glu Arg Glu Glu Trp Ala Gly Phe Arg Ala Arg Glu Thr Ala Ala
        50                  55                  60 ctg gaa gcg gta act gcg cca tcc acc gtt atc gct aca ggc ggc ggc      240
Leu Glu Ala Val Thr Ala Pro Ser Thr Val Ile Ala Thr Gly Gly Gly
65                  70                  75                  80 att att ctg acg gaa ttt aat cgt cac ttc atg caa aat aac ggg atc      288
Ile Ile Leu Thr Glu Phe Asn Arg His Phe Met Gln Asn Asn Gly Ile
                85                  90                  95 gtg gtt tat ttg tgt gcg cca gta tca gtc ctg gtt aac cga ctg caa      336
Val Val Tyr Leu Cys Ala Pro Val Ser Val Leu Val Asn Arg Leu Gln
                100                 105                 110 gct gca ccg gaa gaa gat tta cgg cca acc tta acg gga aaa ccg ctg      384
Ala Ala Pro Glu Glu Asp Leu Arg Pro Thr Leu Thr Gly Lys Pro Leu
            115                 120                 125 agc gaa gaa gtt cag gaa gtg ctg gaa gaa cgc gat gcg cta tat cgc      432
Ser Glu Glu Val Gln Glu Val Leu Glu Glu Arg Asp Ala Leu Tyr Arg
        130                 135                 140 gaa gtt gcg cat att atc atc gac gca aca aac gaa ccc agc cag gtg      480
Glu Val Ala His Ile Ile Ile Asp Ala Thr Asn Glu Pro Ser Gln Val
145                 150                 155                 160 att tct gaa att cgc agc gcc ctg gca cag acg atc aat tgt tga          525
Ile Ser Glu Ile Arg Ser Ala Leu Ala Gln Thr Ile Asn Cys
                165                 170

<210> SEQ ID NO 39
<211> LENGTH: 174
<212> TYPE: PRT
<213> ORGANISM: Eschericha coli
```

<400> SEQUENCE: 39

```
Met Thr Gln Pro Leu Phe Leu Ile Gly Pro Arg Gly Cys Gly Lys Thr
1               5                   10                  15

Thr Val Gly Met Ala Leu Ala Asp Ser Leu Asn Arg Arg Phe Val Asp
            20                  25                  30

Thr Asp Gln Trp Leu Gln Ser Gln Leu Asn Met Thr Val Ala Glu Ile
        35                  40                  45

Val Glu Arg Glu Glu Trp Ala Gly Phe Arg Ala Arg Glu Thr Ala Ala
50                  55                  60

Leu Glu Ala Val Thr Ala Pro Ser Thr Val Ile Ala Thr Gly Gly Gly
65                  70                  75                  80

Ile Ile Leu Thr Glu Phe Asn Arg His Phe Met Gln Asn Asn Gly Ile
                85                  90                  95

Val Val Tyr Leu Cys Ala Pro Val Ser Val Leu Val Asn Arg Leu Gln
            100                 105                 110

Ala Ala Pro Glu Glu Asp Leu Arg Pro Thr Leu Thr Gly Lys Pro Leu
        115                 120                 125

Ser Glu Glu Val Gln Glu Val Leu Glu Arg Asp Ala Leu Tyr Arg
130                 135                 140

Glu Val Ala His Ile Ile Ile Asp Ala Thr Asn Glu Pro Ser Gln Val
145                 150                 155                 160

Ile Ser Glu Ile Arg Ser Ala Leu Ala Gln Thr Ile Asn Cys
                165                 170
```

<210> SEQ ID NO 40
<211> LENGTH: 1161
<212> TYPE: DNA
<213> ORGANISM: Eschericha coli
<220> FEATURE:
<221> NAME/KEY: CDS
<222> LOCATION: (1)..(1161)

<400> SEQUENCE: 40

```
atg aca tcg gaa aac ccg tta ctg gcg ctg cga gag aaa atc agc gcg    48
Met Thr Ser Glu Asn Pro Leu Leu Ala Leu Arg Glu Lys Ile Ser Ala
1               5                   10                  15 ctg gat gaa aaa tta tta gcg tta ctg gca gaa cgg cgc gaa ctg gcc    96
Leu Asp Glu Lys Leu Leu Ala Leu Leu Ala Glu Arg Arg Glu Leu Ala
            20                  25                  30 gtc gag gtg gga aaa gcc aaa ctg ctc tcg cat cgc ccg gta cgt gat   144
Val Glu Val Gly Lys Ala Lys Leu Leu Ser His Arg Pro Val Arg Asp
        35                  40                  45 att gat cgt gaa cgc gat ttg ctg gaa aga tta att acg ctc ggt aaa   192
Ile Asp Arg Glu Arg Asp Leu Leu Glu Arg Leu Ile Thr Leu Gly Lys
50                  55                  60 gcg cac cat ctg gac gcc cat tac att act cgc ctg ttc cag ctc atc   240
Ala His His Leu Asp Ala His Tyr Ile Thr Arg Leu Phe Gln Leu Ile
65                  70                  75                  80 att gaa gat tcc gta tta act cag cag gct ttg ctc caa caa cat ctc   288
Ile Glu Asp Ser Val Leu Thr Gln Gln Ala Leu Leu Gln Gln His Leu
                85                  90                  95 aat aaa att aat ccg cac tca gca cgc atc gct ttt ctc ggc ccc aaa   336
Asn Lys Ile Asn Pro His Ser Ala Arg Ile Ala Phe Leu Gly Pro Lys
            100                 105                 110 ggt tct tat tcc cat ctt gcg gcg cgc cag tat gct gcc cgt cac ttt   384
Gly Ser Tyr Ser His Leu Ala Ala Arg Gln Tyr Ala Ala Arg His Phe
        115                 120                 125 gag caa ttc att gaa agt ggc tgc gcc aaa ttt gcc gat att ttt aat   432
Glu Gln Phe Ile Glu Ser Gly Cys Ala Lys Phe Ala Asp Ile Phe Asn
```

```
                    130                 135                 140
cag gtg gaa acc ggc cag gcc gac tat gcc gtc gta ccg att gaa aat       480
Gln Val Glu Thr Gly Gln Ala Asp Tyr Ala Val Val Pro Ile Glu Asn
145                 150                 155                 160 acc agc tcc ggt gcc ata aac gac gtt tac gat ctg ctg caa cat acc       528
Thr Ser Ser Gly Ala Ile Asn Asp Val Tyr Asp Leu Leu Gln His Thr
                165                 170                 175 agc ttg tcg att gtt ggc gag atg acg tta act atc gac cat tgt ttg       576
Ser Leu Ser Ile Val Gly Glu Met Thr Leu Thr Ile Asp His Cys Leu
            180                 185                 190 ttg gtc tcc ggc act act gat tta tcc acc atc aat acg gtc tac agc       624
Leu Val Ser Gly Thr Thr Asp Leu Ser Thr Ile Asn Thr Val Tyr Ser
        195                 200                 205 cat ccg cag cca ttc cag caa tgc agc aaa ttc ctt aat cgt tat ccg       672
His Pro Gln Pro Phe Gln Gln Cys Ser Lys Phe Leu Asn Arg Tyr Pro
    210                 215                 220 cac tgg aag att gaa tat acc gaa agt acg tct gcg gca atg gaa aag       720
His Trp Lys Ile Glu Tyr Thr Glu Ser Thr Ser Ala Ala Met Glu Lys
225                 230                 235                 240 gtt gca cag gca aaa tca ccg cat gtt gct gcg ttg gga agc gaa gct       768
Val Ala Gln Ala Lys Ser Pro His Val Ala Ala Leu Gly Ser Glu Ala
                245                 250                 255 ggc ggc act ttg tac ggt ttg cag gta ctg gag cgt att gaa gca aat       816
Gly Gly Thr Leu Tyr Gly Leu Gln Val Leu Glu Arg Ile Glu Ala Asn
            260                 265                 270 cag cga caa aac ttc acc cga ttt gtg gtg ttg gcg cgt aaa gcc att       864
Gln Arg Gln Asn Phe Thr Arg Phe Val Val Leu Ala Arg Lys Ala Ile
        275                 280                 285 aac gtg tct gat cag gtt ccg gcg aaa acc acg ttg tta atg gcg acc       912
Asn Val Ser Asp Gln Val Pro Ala Lys Thr Thr Leu Leu Met Ala Thr
    290                 295                 300 ggg caa caa gcc ggt gcg ctg gtt gaa gcg ttg ctg gta ctg cgc aac       960
Gly Gln Gln Ala Gly Ala Leu Val Glu Ala Leu Leu Val Leu Arg Asn
305                 310                 315                 320 cac aat ctg att atg acc cgt ctg gaa tca cgc ccg att cac ggt aat      1008
His Asn Leu Ile Met Thr Arg Leu Glu Ser Arg Pro Ile His Gly Asn
                325                 330                 335 cca tgg gaa gag atg ttc tat ctg gat att cag gcc aat ctt gaa tca      1056
Pro Trp Glu Glu Met Phe Tyr Leu Asp Ile Gln Ala Asn Leu Glu Ser
            340                 345                 350 gcg gaa atg caa aaa gca ttg aaa gag tta ggg gaa atc acc cgt tca      1104
Ala Glu Met Gln Lys Ala Leu Lys Glu Leu Gly Glu Ile Thr Arg Ser
        355                 360                 365 atg aag gta ttg ggc tgt tac cca agt gag aac gta gtg cct gtt gat      1152
Met Lys Val Leu Gly Cys Tyr Pro Ser Glu Asn Val Val Pro Val Asp
    370                 375                 380 cca acc tga                                                          1161
Pro Thr
385

<210> SEQ ID NO 41
<211> LENGTH: 386
<212> TYPE: PRT
<213> ORGANISM: Eschericha coli

<400> SEQUENCE: 41

Met Thr Ser Glu Asn Pro Leu Leu Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30
```

-continued

```
Val Glu Val Gly Lys Ala Lys Leu Leu Ser His Arg Pro Val Arg Asp
             35                  40                  45
Ile Asp Arg Glu Arg Asp Leu Leu Glu Arg Leu Ile Thr Leu Gly Lys
 50                  55                  60
Ala His His Leu Asp Ala His Tyr Ile Thr Arg Leu Phe Gln Leu Ile
 65                  70                  75                  80
Ile Glu Asp Ser Val Leu Thr Gln Gln Ala Leu Leu Gln Gln His Leu
                 85                  90                  95
Asn Lys Ile Asn Pro His Ser Ala Arg Ile Ala Phe Leu Gly Pro Lys
            100                 105                 110
Gly Ser Tyr Ser His Leu Ala Ala Arg Gln Tyr Ala Ala Arg His Phe
        115                 120                 125
Glu Gln Phe Ile Glu Ser Gly Cys Ala Lys Phe Ala Asp Ile Phe Asn
130                 135                 140
Gln Val Glu Thr Gly Gln Ala Asp Tyr Ala Val Val Pro Ile Glu Asn
145                 150                 155                 160
Thr Ser Ser Gly Ala Ile Asn Asp Val Tyr Asp Leu Leu Gln His Thr
                165                 170                 175
Ser Leu Ser Ile Val Gly Glu Met Thr Leu Thr Ile Asp His Cys Leu
            180                 185                 190
Leu Val Ser Gly Thr Thr Asp Leu Ser Thr Ile Asn Thr Val Tyr Ser
        195                 200                 205
His Pro Gln Pro Phe Gln Gln Cys Ser Lys Phe Leu Asn Arg Tyr Pro
210                 215                 220
His Trp Lys Ile Glu Tyr Thr Glu Ser Thr Ser Ala Ala Met Glu Lys
225                 230                 235                 240
Val Ala Gln Ala Lys Ser Pro His Val Ala Ala Leu Gly Ser Glu Ala
                245                 250                 255
Gly Gly Thr Leu Tyr Gly Leu Gln Val Leu Glu Arg Ile Glu Ala Asn
            260                 265                 270
Gln Arg Gln Asn Phe Thr Arg Phe Val Val Leu Ala Arg Lys Ala Ile
        275                 280                 285
Asn Val Ser Asp Gln Val Pro Ala Lys Thr Thr Leu Leu Met Ala Thr
290                 295                 300
Gly Gln Gln Ala Gly Ala Leu Val Glu Ala Leu Leu Val Leu Arg Asn
305                 310                 315                 320
His Asn Leu Ile Met Thr Arg Leu Glu Ser Arg Pro Ile His Gly Asn
                325                 330                 335
Pro Trp Glu Glu Met Phe Tyr Leu Asp Ile Gln Ala Asn Leu Glu Ser
            340                 345                 350
Ala Glu Met Gln Lys Ala Leu Lys Glu Leu Gly Glu Ile Thr Arg Ser
        355                 360                 365
Met Lys Val Leu Gly Cys Tyr Pro Ser Glu Asn Val Val Pro Val Asp
370                 375                 380
Pro Thr
385
```